US 11,864,866 B2

(12) United States Patent
Beldon et al.

(10) Patent No.: US 11,864,866 B2
(45) Date of Patent: Jan. 9, 2024

(54) METHOD AND APPARATUS FOR MEASURING LIGHT INTENSITY FOR IMAGING

(71) Applicant: Cortirio Limited, Sedgefield (GB)

(72) Inventors: Patrick John Beldon, London (GB); Paul David Macey, London (GB)

(73) Assignee: Cortirio Limited, Sedgefield (GB)

( * ) Notice: Subject to any disclaimer, the term of this patent is extended or adjusted under 35 U.S.C. 154(b) by 413 days.

(21) Appl. No.: 17/296,023

(22) PCT Filed: Dec. 4, 2019

(86) PCT No.: PCT/GB2019/053424
§ 371 (c)(1),
(2) Date: May 21, 2021

(87) PCT Pub. No.: WO2020/115477
PCT Pub. Date: Jun. 11, 2020

(65) Prior Publication Data
US 2022/0031167 A1 Feb. 3, 2022

(30) Foreign Application Priority Data

Dec. 5, 2018 (GB) .................................... 1819847

(51) Int. Cl.
*A61B 5/00* (2006.01)
*G01J 1/16* (2006.01)
(Continued)

(52) U.S. Cl.
CPC .............. *A61B 5/0075* (2013.01); *G01J 1/16* (2013.01); *G01J 1/4228* (2013.01); *G01J 3/2823* (2013.01); *G01J 2001/446* (2013.01)

(58) Field of Classification Search
None
See application file for complete search history.

(56) References Cited

U.S. PATENT DOCUMENTS 4,032,801 A 6/1977 Fulkerson
4,410,804 A * 10/1983 Stauffer ................. G06V 20/64
348/42
(Continued)

FOREIGN PATENT DOCUMENTS

CN 106248559 A 12/2016

OTHER PUBLICATIONS

Anonymous: "Common mode rejection ratio of a balanced detector | Koheron", Mar. 13, 2017, XP055667510,https://www.koheron.com/blog/2017/03/13/common-mode-rejection-ratio-measurement.
(Continued)

*Primary Examiner* — Marcus H Taningco
(74) *Attorney, Agent, or Firm* — Burns & Levinson LLP; Daniel McGrath

(57) ABSTRACT

A method of measuring light intensity for imaging using a light detector array comprising a plurality of light detectors arranged to generate an output corresponding to an intensity of incident light. In a first measurement mode the light detector array generates a first plurality of output signals, each generated by one group of proximate light detectors, each group comprising a light detector pair, the first plurality of output signals each corresponding to a difference between the light intensity detected by the light detectors of the group, and generating a light intensity measurement for each group from each received output signal of the first plurality of output signals. In a second measurement mode the light detector array generates a second plurality of output signals, and a light intensity measurement is generated for each light detector from the second plurality of output signals.

37 Claims, 21 Drawing Sheets

(51) Int. Cl.
*G01J 1/42* (2006.01)
*G01J 3/28* (2006.01)
*G01J 1/44* (2006.01)

(56) References Cited

U.S. PATENT DOCUMENTS

| | | | | |
|---|---|---|---|---|
| 5,410,145 | A | * 4/1995 | Coroy | H03F 3/087 |
| | | | | 257/E27.127 |
| 5,834,765 | A | 11/1998 | Ashdown | |
| 7,602,942 | B2 | * 10/2009 | Bazakos | G06V 40/166 |
| | | | | 382/103 |
| 2019/0274548 | A1 | * 9/2019 | Alford | A61B 5/4064 |
| 2019/0294024 | A1 | * 9/2019 | Koehler | G02F 1/2255 |

OTHER PUBLICATIONS

Anonymous: "Signal Diode and Switching Diode Characteristics", Mar. 12, 2018, XP055667262, https://www.electronics-tutorials.ws/diode/diode_4.html.

International Search Report and Written Opinion for PCT Application No. PCT/GB2019/053424 dated Feb. 20, 2020.

Search Report of GB Application No. GB1819847.3 dated Mar. 14, 2019.

* cited by examiner

"Relative" measurement configuration

First "absolute" measurement configuration

Second "absolute" measurement configuration

"Relative" measurement configuration

Voltage ladder "Relative" measurement configuration method 1

Voltage ladder "Relative" measurement configuration method 2

Second absolute configuration

METHOD AND APPARATUS FOR MEASURING LIGHT INTENSITY FOR IMAGING

TECHNICAL FIELD

The present invention relates to techniques for measuring light intensity in imaging applications.

BACKGROUND

Near-infrared spectroscopy techniques for medical imaging, in particular for cranial imaging are known. Such techniques can be used to measure oxygenation and microvascular function and can therefore be used to detect and assess issues such as intra-cranial hematomas.

Typically, near-infrared spectroscopy scanners use an array of high-powered light emitters to direct light into the cranium of a subject and then measure corresponding light detected at an array of light detectors. Imaging information can be generated from the detected light which enables information about the condition of the cranial space (such as the presence and extent of a hematoma) to be determined.

Near-infrared spectroscopy scanners are typically smaller and more portable than other medical scanning technology such as computed tomography (CT) scanners and magnetic resonance imaging (MRI) scanners. Nevertheless, in order to achieve desirable levels of imaging resolution, high-powered light sources must be used to illuminate the subject's head to achieve the light levels necessary to generate useful imaging information.

As a result, use of near-infrared spectroscopy tends to be restricted to places where the necessary equipment (suitable power supplies etc) are found. It is generally necessary to implement near-infrared spectroscopy scanners systems in a fixed location even though it would be desirable to provide near-infrared spectroscopy imaging techniques in a more flexible and mobile implementation.

SUMMARY OF THE INVENTION

In accordance with a first aspect of the invention, there is provided a method of measuring light intensity for imaging using a light detector array comprising a plurality of light detectors, each light detector of the plurality of light detectors arranged to generate an output corresponding to an intensity of incident light. The method comprises, in a first measurement mode: controlling the light detector array to generate a first plurality of output signals, each output signal of the first plurality of output signals generated by one of a plurality of groups of proximate light detectors of the light detector array, each group of proximate light detectors comprising a first light detector and second light detector forming a light detector pair, each output signal of the first plurality of output signals corresponding to a difference between the light intensity detected by the light detectors of the group of proximate light detectors, and generating a light intensity measurement for each group from each received output signal of the first plurality of output signals, the method further comprising, in a second measurement mode: controlling the light detector array to generate a second plurality of output signals, each output signal of the second plurality of output signals generated by one of the light detectors, and generating a light intensity measurement for each light detector from each received output signal of the second plurality of output signals.

Optionally, the light detectors comprise photodiodes.

Optionally, the photodiodes of the light detector array are arranged in a linear array.

Optionally, each light detector pair comprise a photodiode pair comprising a first photodiode in series with a second photodiode.

Optionally, the anode and cathode of each photodiode are connected, via a switching matrix to a plurality of voltage lines and measurement lines to implement the first and second measurement mode.

Optionally, the linear array of light detectors comprises a plurality of photodiode pairs connected in series.

Optionally, a cathode of the first photodiode of each photodiode pair is connected to an anode of the second photodiode of each pair.

Optionally, the photodiode pairs of the linear array are arranged in sequentially forward and reverse polarity.

Optionally, the first measurement mode is implemented by: holding each photodiode pair in a reverse bias state where a first bias voltage Vbn is applied to an anode of the first photodiode of the photodiode pair and a second bias voltage Vbp is applied to a cathode of the second photodiode of the photodiode pair, and a measurement voltage Vm is applied at the cathode of the first photodiode connected to the anode of the second photodiode, said measurement voltage a voltage level between the first bias voltage and second bias voltage, and measuring an output of each photodiode pair corresponding to a difference in the light detected of the photodiode pair by measuring the current output at the cathode of the first photodiode connected to the anode of the second photodiode.

Optionally, the second measurement mode is implemented by: applying a null voltage Vbx to the anode of the first photodiode of each pair thereby holding the first photodiode of each pair in an unbiased, non-conducting state, and applying the second bias voltage Vbp to the cathode of the second photodiode of each pair and applying the measurement voltage Vm at the cathode of the first photodiode connected to the anode of the second photodiode, thereby holding the second photodiode of each photodiode pair in a reverse bias state, and measuring an output of the second photodiode of each photodiode pair from the current output measured at the cathode of the first photodiode connected to the anode of the second photodiode, and, before or subsequently applying a first bias voltage Vbn to the anode of the first photodiode of each pair and applying the measurement voltage Vm at the cathode of the first photodiode connected to the anode of the second photodiode thereby holding the first photodiode of each pair in a reverse biased state, and applying a null voltage Vbx to the cathode of the second photodiode of each photodiode pair thereby holding the second photodiode of each photodiode pair in an unbiased, non-conducting state, and measuring an output of the second photodiode of each photodiode pair from the current output measured at the cathode of the first photodiode connected to the anode of the second photodiode.

Optionally, the photodiode pairs of the linear array are arranged with the same polarity.

Optionally, the first measurement mode is implemented by: holding each photodiode pair in a null bias state where a zero voltage bias is applied to the anode and cathode of each of photodiode, and measuring an output of each photodiode pair corresponding to a difference in the light detected of the photodiode pair by measuring the current output at the cathode of the first photodiode connected to the anode of the second photodiode.

Optionally, the first mode is implemented by: holding each photodiode pair in a reverse bias state where a sequentially increasing voltage bias is applied to the anode of each adjacent photodiode, and measuring an output of each photodiode pair corresponding to a difference in the light detected of the photodiode pair by measuring the current output at the cathode of the first photodiode connected to the anode of the second photodiode.

Optionally, the second measurement mode is implemented by: applying a first bias voltage to the anode of first photodiode of each pair; applying the first bias voltage to the cathode of the first diode of each pair and the anode of the second photodiode of each pair, thereby holding the first photodiode of each pair in an unbiased, non-conducting state, wherein the first bias voltage sequentially increases along the photodiode array for each photodiode pair thereby holding the second photodiode of each pair in a reverse bias state, and measuring an output of the second photodiode of each photodiode pair from the current output measured at the cathode of the first photodiode connected to the anode of the second photodiode, and, before or subsequently applying the first bias voltage to the cathode of the second photodiode of each pair; applying the same bias voltage to the cathode of the first diode of each pair and the anode of the second photodiode of each pair, thereby holding the second photodiode of each pair in an unbiased, non-conducting state, wherein the second bias voltage sequentially increases along the photodiode array for each photodiode pair thereby holding the first photodiode of each pair in a reverse bias state, and measuring an output of the first photodiode of each photodiode pair from the current output measured at the cathode of the first photodiode connected to the anode of the second photodiode.

Optionally, the method further comprises applying the requisite voltages to the anodes and cathodes of the photodiodes by connecting the anodes and cathodes of the photodiodes to a plurality of voltage lines, each voltage line held at one of the requisite voltages.

Optionally, the anodes and cathodes of the photodiodes are connectable to the requisite voltage lines via a switching matrix.

Optionally, each voltage line is connected to a programmable voltage supply arranged to provide for each photodiode pair and for each photodiode a voltage level corresponding to the first bias voltage Vbn or second bias voltage Vbp, the first bias voltage Vbn and second bias voltage Vbp determined for each photodiode pair and for each photodiode in accordance with a calibration technique.

Optionally, the calibration technique comprises: applying reference illumination to each photodiode and each photodiode pair, determining, for operation in the first measurement mode, the first and second bias voltages by determining first and second voltages necessary to generate a reference output current corresponding to the reference illumination, and determining for operation in the second measurement mode, first and second bias voltages necessary to generate a reference output current corresponding to the reference illumination.

Optionally, one or more of the first and second bias voltages necessary to generate a reference output current corresponding to the reference illumination for operation in the first measurement mode, and/or one or more of the first and second bias voltages necessary to generate a reference output current corresponding to the reference illumination for operation in the second measurement mode are provided by the programmable voltage supplies by modulating between a first and second voltage level.

Optionally, the method further comprises generating near-infrared spectroscopy imaging data using the light intensity measurements.

In accordance with a second aspect of the invention, there is provided: a light detector array comprising a plurality of light detectors, each light detector of the plurality of light detectors operable to generate an output corresponding to an intensity of incident light, said apparatus comprising means to control the plurality of light detectors, in a first measurement mode: to generate a first plurality of output signals, each output signal of the first plurality of output signals generated by one of a plurality of groups of proximate light detectors of the light detector array, wherein each group of proximate light detectors comprises a first light detector and second light detector forming a light detector pair, each output signal of the first plurality of output signals corresponding to a difference between the light intensity detected by the light detectors of the group of proximate light detectors, said apparatus further comprising a light intensity measurement unit arranged to generate a light intensity measurement for each group from each received output signal of the first plurality of output signals, wherein the means to control the plurality of light detectors is operable, in a second measurement mode: to control the plurality of light detectors to generate a second plurality of output signals, each output signal of the second plurality of output signals generated by one of the light detectors, and the light intensity measurement unit is arranged to generate a light intensity measurement for each light detector from each received output signal of the second plurality of output signals.

Optionally, the light detectors comprise photodiodes.

Optionally, the photodiodes of the light detector array are arranged in a linear array.

Optionally, each light detector pair comprise a photodiode pair comprising a first photodiode in series with a second photodiode.

Optionally, the anode and cathode of each photodiode are connected, via a switching matrix to a plurality of voltage lines and measurement lines to implement the first and second measurement mode.

Optionally, the linear array of light detectors comprises a plurality of photodiode pairs connected in series.

Optionally, a cathode of the first photodiode of each photodiode pair is connected to an anode of the second photodiode of each pair.

Optionally, the photodiode pairs of the linear array are arranged in sequentially forward and reverse polarity.

Optionally, the first measurement mode is implemented by the means to control the plurality of light detectors: holding each photodiode pair in a reverse bias state where a first bias voltage Vbn is applied to an anode of the first photodiode of the photodiode pair and a second bias voltage Vbp is applied to a cathode of the second photodiode of the photodiode pair, and a measurement voltage Vm is applied at the cathode of the first photodiode connected to the anode of the second photodiode said measurement voltage a voltage level between the first bias voltage and second bias voltage, and the light intensity measurement unit is arranged to measure an output of each photodiode pair corresponding to a difference in the light detected of the photodiode pair by measuring the current output at the cathode of the first photodiode connected to the anode of the second photodiode.

Optionally, the second measurement mode is implemented by the means to control the plurality of light detectors: applying a null voltage Vbx to the anode of the first photodiode of each pair thereby holding the first photodiode of each pair in an unbiased, non-conducting state, and applying the second bias voltage Vbp to the cathode of the second photodiode of each pair and applying the measurement voltage Vm at the cathode of the first photodiode connected to the anode of the second photodiode, thereby holding the second photodiode of each photodiode pair in a reverse bias state, and the light intensity measurement unit is arranged to measure an output of the second photodiode of each photodiode pair from the current output measured at the cathode of the first photodiode connected to the anode of the second photodiode, and, before or subsequently the means to control the plurality of light detectors: applying a first bias voltage Vbn to the anode of the first photodiode of each pair and applying the measurement voltage Vm at the cathode of the first photodiode connected to the anode of the second photodiode thereby holding the first photodiode of each pair in a reverse biased state, and applying a null voltage Vbx to the cathode of the second photodiode of each photodiode pair thereby holding the second photodiode of each photodiode pair in an unbiased, non-conducting state, the light intensity measurement unit is arranged to measure an output of the second photodiode of each photodiode pair from the current output measured at the cathode of the first photodiode connected to the anode of the second photodiode.

Optionally, the photodiode pairs of the linear array are arranged with the same polarity.

Optionally, the first measurement mode is implemented by the means to control the plurality of light detectors: holding each photodiode pair in a null bias state where a zero voltage bias is applied to the anode and cathode of each of photodiode, and the light intensity measurement unit is arranged to measure an output of each photodiode pair corresponding to a difference in the light detected of the photodiode pair by measuring the current output at the cathode of the first photodiode connected to the anode of the second photodiode.

Optionally, the first mode is by the means to control the plurality of light detectors: holding each photodiode pair in a reverse bias state where a sequentially increasing voltage bias is applied to the anode of each adjacent photodiode, and the light intensity measurement unit is arranged to measure an output of each photodiode pair corresponding to a difference in the light detected of the photodiode pair by measuring the current output at the cathode of the first photodiode connected to the anode of the second photodiode.

Optionally, the second mode is implemented by the means to control the plurality of light detectors: applying a first bias voltage to the anode of first photodiode of each pair; applying the first bias voltage to the cathode of the first diode of each pair and the anode of the second photodiode of each pair, thereby holding the first photodiode of each pair in an unbiased, non-conducting state, wherein the first bias voltage sequentially increases along the photodiode array for each photodiode pair thereby holding the second photodiode of each pair in a reverse bias state, and the light intensity measurement unit is arranged to measure an output of the second photodiode of each photodiode pair from the current output measured at the cathode of the first photodiode connected to the anode of the second photodiode, and, before or subsequently and, before or subsequently the means to control the plurality of light detectors: applying the first bias voltage to the cathode of the second photodiode of each pair; applying the same bias voltage to the cathode of the first diode of each pair and the anode of the second photodiode of each pair, thereby holding the second photodiode of each pair in an unbiased, non-conducting state, wherein the second bias voltage sequentially increases along the photodiode array for each photodiode pair thereby holding the first photodiode of each pair in a reverse bias state, and the light intensity measurement unit is arranged to measure an output of the first photodiode of each photodiode pair from the current output measured at the cathode of the first photodiode connected to the anode of the second photodiode.

Optionally, the means to control the plurality of light detectors is operable to apply the requisite voltages to the anodes and cathodes of the photodiodes by connecting the anodes and cathodes of the photodiodes to a plurality of voltage lines, each voltage line held at one of the requisite voltages.

Optionally, the means to control the plurality of light detectors comprises a switching matrix controlled by a control unit.

According to a third aspect of the invention, there is provided a near-infrared spectroscopy system for imaging a subject's head comprising an imaging apparatus according to the second aspect.

According to certain examples, there is provided a method of calibrating an imaging apparatus, said imaging apparatus comprising: a photodiode array comprising a plurality of photodiodes, said apparatus comprising means to control the plurality of photodiodes, in use, in a first measurement mode: to generate a plurality of output currents, each output current generated by one of a plurality of pairs of adjacent photodiodes, each output current corresponding to a difference between the light intensity detected by the photodiodes of the photodiode pair, wherein the first measurement mode is implemented by the means to control the plurality of photodiodes: holding each photodiode pair in a reverse bias state where a first bias voltage Vbn is applied to an anode of the first photodiode of the photodiode pair and a second bias voltage Vbp is applied to a cathode of the second photodiode of the photodiode pair, and a measurement voltage Vm is applied at the cathode of the first photodiode connected to the anode of the second photodiode said measurement voltage a voltage level between the first bias voltage and second bias voltage, wherein the calibration technique comprises: applying reference illumination to each photodiode pair, and determining for each photodiode pair the first and second bias voltages by determining first bias voltage Vbn and second bias voltage Vbp necessary to generate a reference output current corresponding to the reference illumination.

Optionally, said apparatus comprises means to control the plurality of photodiodes, in use, in a second measurement mode: to generate a further plurality of output signals, each output signal generated by one of the photodiodes, wherein the second measurement mode is implemented by applying a null voltage Vbx to the anode of the first photodiode of each pair thereby holding the first photodiode of each pair in an unbiased, non-conducting state, and applying the second bias voltage Vbp to the cathode of the second photodiode of each pair and applying the measurement voltage Vm at the cathode of the first photodiode connected to the anode of the second photodiode, thereby holding the second photodiode of each photodiode pair in a reverse bias state, and, before or subsequently applying a first bias voltage Vbn to the anode of the first photodiode of each pair and the measurement voltage Vm at the cathode of the first photodiode connected to the anode of the second photodiode thereby holding the first photodiode of each pair in a reverse biased state, and applying a null voltage Vbx to the cathode of the second photodiode of each photodiode pair thereby holding the second photodiode of each photodiode pair in an unbiased, non-conducting state, wherein the calibration technique further comprises: applying reference illumination to each photodiode pair, and for each photodiode pair: applying a null voltage to the anode of the first photodiode of the photodiode pair and determining the second bias voltage Vbp necessary to be applied to the cathode of the second photodiode necessary to generate a reference output from the second photodiode corresponding to the reference illumination, and before or subsequently, applying a null voltage to the cathode of the second photodiode of the photodiode pair and determining the first bias voltage Vbn necessary to be applied to the anode of the first photodiode necessary to generate a reference output from the first photodiode corresponding to the reference illumination.

Optionally, determining the first bias voltage and the second bias voltage for each photodiode pair comprises modulating between a first voltage level and a second voltage level of a plurality of predetermined voltage levels.

In accordance with embodiments of the invention, a technique is provided for measuring light intensity in imaging applications, and in particular near-infrared spectroscopy medical imaging applications. In accordance with the technique a measurement mode is provided whereby the output signals from light detectors of an array, for example an array comprising a plurality of adjacent photodiodes forming light detector pairs, are measured by comparing their "relative" outputs (that is the difference between the measurement of incident light generated between adjacent light detectors) rather than their individual outputs.

Generating light intensity measurements for imaging by comparing "relative" output of adjacent light detectors allows improved resolution imaging to be performed, particularly for near-infrared spectroscopy medical imaging applications where the difference in incident light tends to be small from pixel to pixel. Generating imaging data based on the difference in light intensity between light detectors rather than the "absolute" light intensity detected by each light detector allows these small differences to be more accurately detected thus improving the overall resolution of the system.

Furthermore, a higher density photodiode array can be more usefully used because differences in detected light intensity that would otherwise be lost as noise if the output of each light detector was processed individually (due to the closer proximity of light detectors) can be more readily detected.

The technique further includes use of a second measurement mode in which the output signal from each light detector are individually measured. In this measurement mode large differences between pixels can be more accurately detected. By providing this second measurement mode, composite imaging data can be generated which includes imaging data generated using the first measurement mode (to identify fine detail where light intensity varies a smaller amount from pixel to pixel) and imaging data generated using the second measurement mode (to more accurately represent regions where larger differences exist, for examples edges and so on).

In accordance with certain embodiments of the invention, different configurations can be used to implement the "relative" measurement mode and the "absolute" measurement mode. In certain examples, photodiodes of the photodiode array are arranged in series in a linear array. In certain embodiments, the photodiodes are connected directly to each other in series. In certain embodiments, the photodiodes are connected via switching elements, for example in a switching matrix. In certain examples the photodiode array is divided into pairs of adjacent photodiodes. In certain examples, the polarity of the photodiodes pairs alternates along the array. In certain examples changing between the "relative" and "absolute" measurement mode comprises applying suitable bias voltages to the photodiodes of the array.

Various further features and aspects of the invention are defined in the claims.

BRIEF DESCRIPTION OF DRAWINGS

Embodiments of the present invention will now be described by way of example only with reference to the accompanying drawings where like parts are provided with corresponding reference numerals and in which.

DETAILED DESCRIPTION

Figure 1:
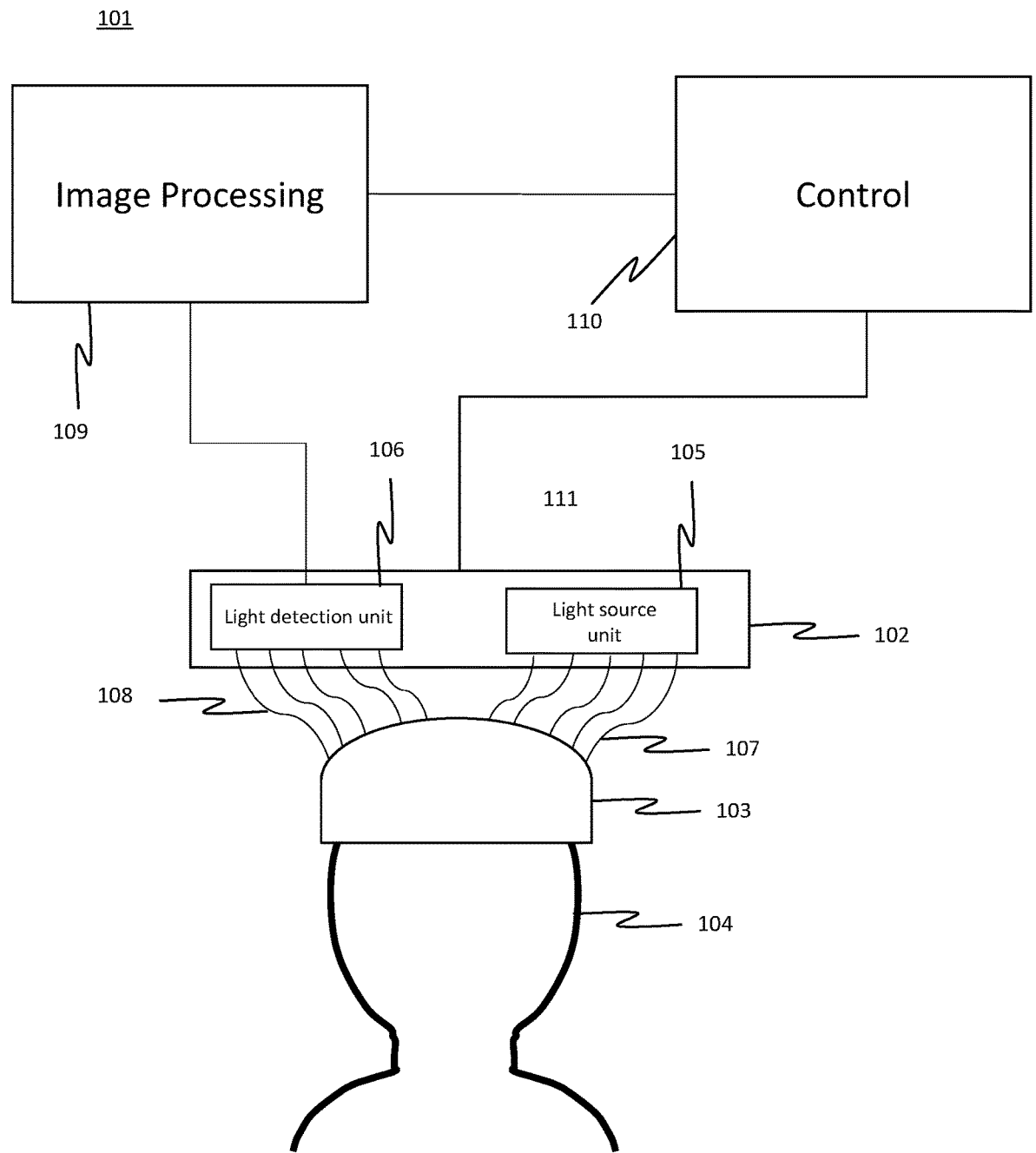
FIG. 1 provides a simplified schematic diagram of a near-infrared spectroscopy apparatus 101 for performing imaging operations on a subject in accordance with certain embodiments of the invention.

FIG. 1 provides a simplified schematic diagram of a near-infrared spectroscopy apparatus 101 for performing imaging operations on a subject.

The apparatus 101 comprises a headset connected to a measurement module 102. The measurement module 102 comprises a light source unit 105, a light detection unit 106. In use, the head set 103 is fitted over the head 104 of a subject.

The light source unit 105 comprises an array of light emitters, typically an array of light emitting photodiodes (LEDs). The LEDs may be of the same type or may be of different type, for example, two or three different types, producing different wavelengths of light.

It will be understood that "light" in the context of embodiments of the invention, refers generally to electromagnetic radiation within the frequency range typically used in near-infrared spectroscopy applications.

The measurement module 102 further comprises a first set of light conduits 107 referred to as "optodes". At a first end, each optode of the first set of optodes 107 is optically coupled to one of the LEDs of the LED array of the light source unit 105. Each optode of the first set of optodes 107 extends away from the light source unit 105 and terminates at a second end in the head set 103.

The terminating ends of the optodes of the first set of optodes are positioned so that light from the LEDs is directed into a particular region of the head 104 of the subject.

The measurement module 102 further comprises a second set of optodes 108. At a first end, each optode of the second set of optodes 108 is positioned within the head set 103 to detect light emitted from a particular region of the head 104 of the subject. The light detection unit 106 comprises an array of light detectors, typically provided by an array of photodiodes. Each optode of the second set of optodes 108 extends away from the headset 103 and terminates at a connection at the light detection unit 106 which optically couples the optode to one of the photodiodes.

The measurement module 102, and the imaging processing module 109 are connected to a control module 110 which controls operation of the apparatus 101.

In use, light is directed into the head 104 of the subject from the first set of optodes 107 and corresponding light emitted from the head 104 of the subject is transmitted via the second set of optodes 108 to the light detection unit 106.

Typically, the output of each LED is modulated, that is, the intensity of the light output of each LED varies in accordance with a modulated waveform such as a sine wave. This is typically achieved by driving each LED with a corresponding periodic signal. Typical frequencies of the output of the LED array are between 10 kHz to 10 MHz. Accordingly, the light received by the light detection unit 106 is also modulated.

The light detection unit 106 measures the received light, digitises the measurements and communicates the digitised data to the image processing module. Information relating to the received light is processed by the image processing module 109. Specifically, the image processing module 109 undertakes image processing operations to generate imaging data relating to the internal state within the head 104 of the subject in accordance with near-infrared spectroscopy imaging techniques.

Figure 2:
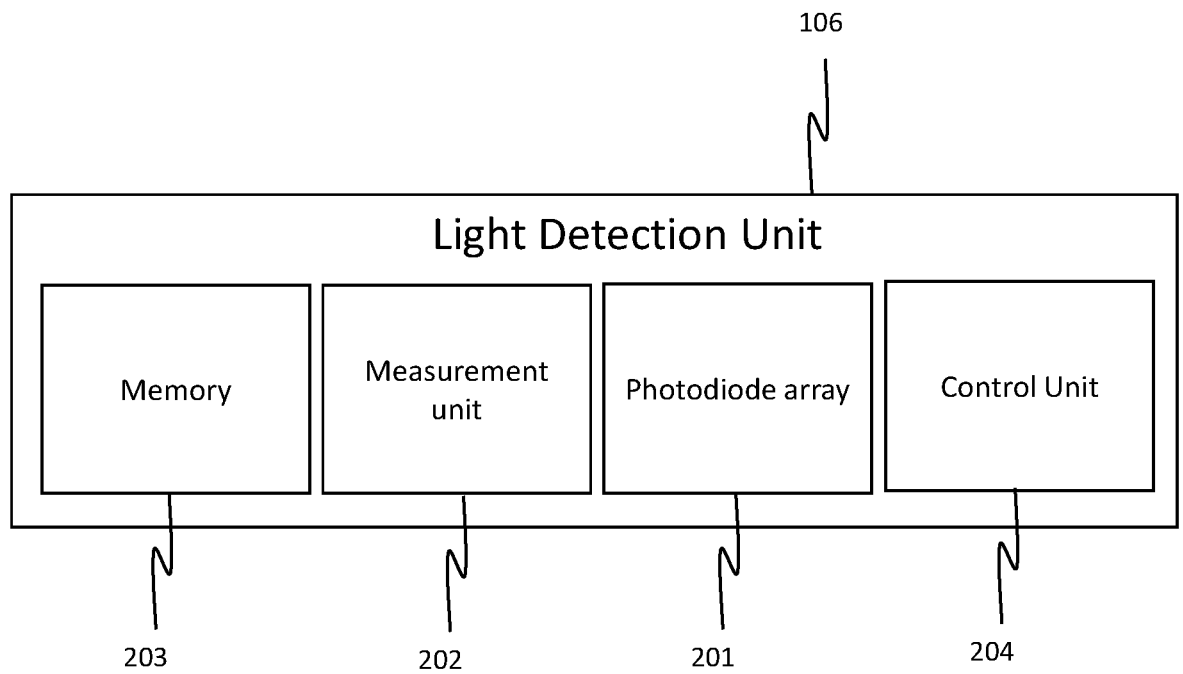
FIG. 2 provides a simplified schematic diagram of a light detection unit in accordance with certain embodiments of the invention.

FIG. 2 provides a more detailed schematic diagram of the light detection unit 106. The light detection unit 106 comprises a photodiode array 201, measurement processing unit 202 memory unit 203 and control unit 204.

Under the control of the control unit 204, the measurement processing unit 202 is arranged to measure the various currents within the photodiode array, digitise them, store them and then communicate the digitised values to the image processing module 109 for image processing.

Conventionally, when measuring the intensity of light incident on an array of photodiodes, during the measurement cycle, each photodiode is held in a reverse bias state, and the current generated by each photodiode when it is exposed to light is individually measured.

However, in accordance with certain embodiments of the invention, the measurement processing unit 202 is arranged to undertake measurements in two modes. In a first mode, the photodiode array is segmented into adjacent photodiode pairs, and a "relative" measurement is taken for each photodiode pair. In the "relative" mode, the difference between the current flowing in the first photodiode and the current flowing in the second photodiode of the photodiode pair is measured.

In a second mode, an "absolute" measurement is taken for each photodiode. That is, a measurement is taken in accordance with conventional techniques as described above, i.e. during a measurement cycle, each individual photodiode is held in a reverse bias, state and the current that is generated is measured.

In certain embodiments, composite images can be generated with measurements generated from both the "relative" mode and the "absolute" mode.

For example, the image processing module 109 generates first imaging data using measurements generated using the "relative" measurement mode, generates second imaging data using measurements generated using the "absolute" measurement mode, and then combines the first imaging data and second imaging data to generate composite imaging data which, for example, includes both fine detail between pixels, and larger differences between pixels, for example edges.

To implement the "relative" measurement mode and the "absolute" measurement mode, as described in more detail below, different physical photodiode array configurations can be used.

In certain embodiments, a photodiode array comprising a plurality of photodiodes connected in series is provided. The photodiode array is divided into a plurality of photodiode pairs by the arrangement of the polarity (i.e. the "direction" in which they are connected) of the photodiodes. The polarity of both photodiodes in each photodiode pair is the same (thus the cathode of one of the photodiode is connected to the anode of the other photodiode of the photodiode pair). However, the polarity of each photodiode pair with respect to the adjacent photodiode pairs alternates (thus the anode of one of the photodiodes of a given photodiode pair is connected to the anode of a photodiode of an adjacent photodiode pair and the cathode of the other of the photodiodes of the given photodiode pair is connected to the cathode of the cathode of a photodiode of an adjacent photodiode pair). A simplified example of this type of photodiode array configuration is described in more detail below with reference to FIG. 4.

In other embodiments, the photodiodes of the photodiode array are connected in series and are all connected with the same polarity (that is the cathode of each photodiode is connected to the anode of an adjacent photodiode). A simplified example of this type of photodiode array configuration is described in more detail below with reference to FIG. 5d.

In both these embodiments, the "relative" measurement mode and "absolute" measurement mode can be implemented by applying certain voltages (voltage configurations) to the photodiode arrays to hold the photodiodes in suitable states.

In further embodiments, the photodiodes of the photodiode array are not directly connected in series, but are instead connected via a switching matrix.

Figure 3:
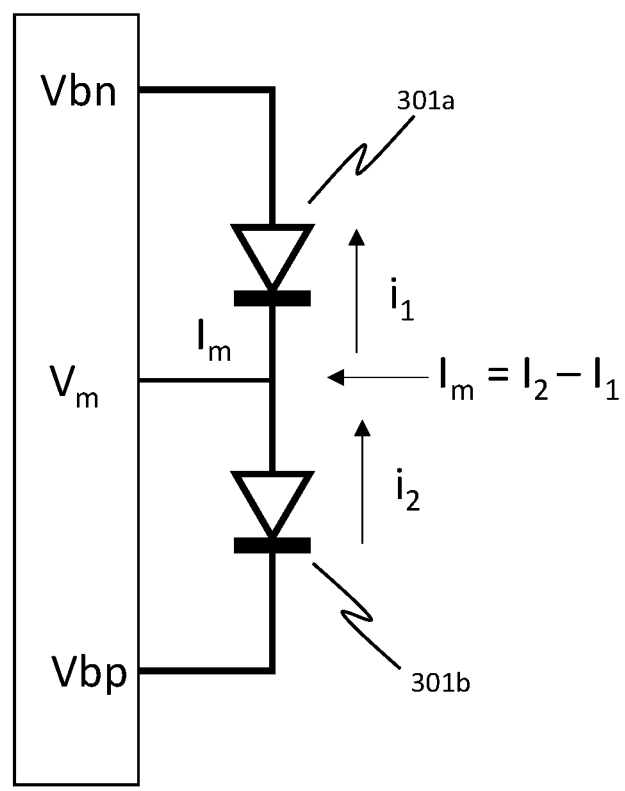
FIG. 3 provides a schematic diagram depicting the concept of a "relative" current measurement mode in accordance with certain embodiments of the invention.

This concept of the operation of the first "relative" measurement mode is depicted schematically in FIG. 3. Specifically, FIG. 3 shows an application of input voltages and associated output currents, which enable the difference in light intensity incident on two adjacent photodiodes, connected in series, to be measured.

FIG. 3 shows a photodiode pair 301 comprising a first photodiode 301a and a second photodiode 301b. The first photodiode 301a and second photodiode 301b are connected in series and a first voltage bias (Vbn) is applied to the anode of the first photodiode 301a and a second voltage bias Vbp is applied to the cathode of the second photodiode.

A third voltage Vm is applied at a measurement node, i.e. the point where the cathode of the first photodiode 301a is connected to the anode of the second photodiode 301b. The voltage $V_m$ is typically half the supply voltage. For example, if the supply voltage is 5V, $V_m$ is typically 2.5V. The voltage $V_m$ is typically halfway between the voltage Vbp and Vbn.

In this way, the photodiode pair is reverse biased (i.e. both photodiodes are reverse biased).

A first current $i_1$ flows through the first photodiode 301a and a second current $i_2$ flows through the second photodiode 301b. A measurement current flows $I_m$ flows at the measurement node which is the difference between the current flowing through the first photodiode 301a and the current flowing through the second photodiode 301b $I_m$.

As described above, the light from each LED of the LED array, and thus the light received by each photodiode received by the photodiodes varies in intensity in accordance with a periodic signal. Accordingly, the current generated by each photodiode, and thus the measurement current $i_m$ is not constant and typically comprises a DC component and an AC component.

Figure 4:
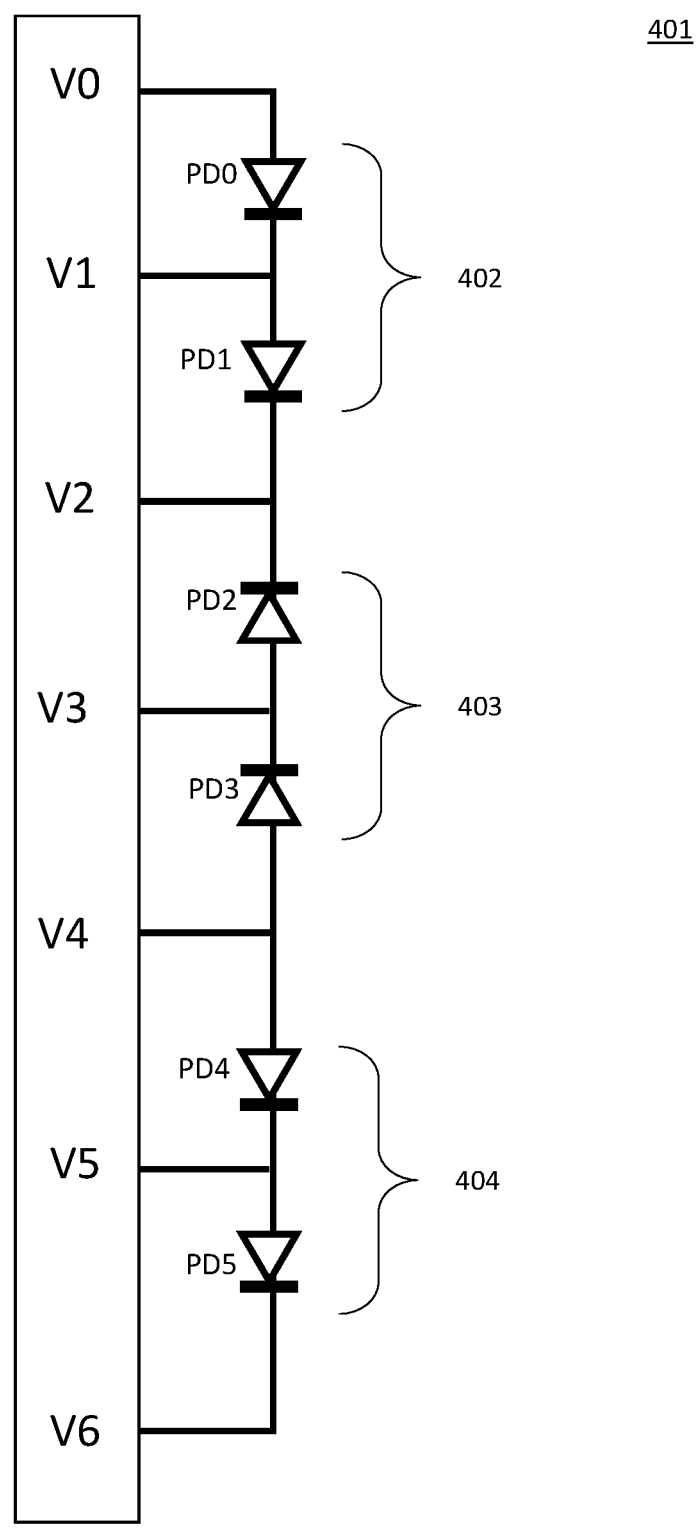
FIG. 4 provides a schematic diagram of a depicting a photodiode array in accordance with certain embodiments of the invention.

FIG. 4 provides a schematic diagram depicting a photodiode array in accordance with certain embodiments which can be adapted to operate in a first "relative" mode and a second "absolute" mode. Specifically, FIG. 4 depicts the physical configuration of a photodiode array in which the photodiodes are connected in series but arranged in photodiode pairs of alternating polarity.

The photodiode array 401 comprises six photodiodes (PD0, PD1, PD2, PD3, PD4, PD5) connected in series.

The photodiode array 401 is divided into 3 photodiode pairs, a first pair 402 comprising the first and second photodiode (PD0 and PD1), a second pair 403 comprising the third and fourth photodiode (PD2 and PD3) and a third pair 404 comprising the fifth and sixth photodiode (PD4 and PD5).

As can be seen from FIG. 4, the cathode of the first photodiode in each pair (PD0, PD3, and PD4) is connected to the anode of the second photodiode in each pair (PD1, PD2 and PD5). However, the polarity of the photodiodes from of the second photodiode pair 403 is reversed in relation to the polarity of the photodiodes from the first photodiode pair 402 and the third photodiode pair 404. That is, the cathode of the second photodiode PD1 is connected to the cathode of the third photodiode PD2 and the anode of the fourth photodiode PD3 is connected to the anode of the fifth photodiode PD4. The photodiode array 401 comprises seven voltage nodes that can be controlled: a first voltage node V0 at the anode of the first photodiode PD0; a second voltage node V1 at the cathode of the first photodiode PD0 and the anode of the second photodiode PD1; a third voltage node V2 at the cathode of the second photodiode PD1 and the cathode of the third photodiode PD2; a fourth voltage node V3 at the anode of the third photodiode PD2 and the cathode of the fourth photodiode PD3; a fifth voltage node V4 at the anode of the fourth photodiode PD3 and the anode of the fifth photodiode PD4; a sixth voltage node V5 at the cathode of the fifth photodiode PD4 and the anode of the sixth photodiode PD5, and a seventh voltage node V6 at the cathode of the sixth photodiode PD5.

In accordance with certain embodiments, the voltage expressed at each node connected to a photodiode anode or photodiode cathode (the voltage configuration) can be controlled in order to change the mode of the array so that it operates in a "relative" measurement mode where the difference in the current flow between the photodiodes in each pair is measured, or an "absolute" measurement mode where the current flow in the first photodiode (PD0), third photodiode (PD2) and fourth photodiode (PD3) photodiode is measured and a second "absolute" measurement configuration where the current flow in second photodiode (PD1), fourth photodiode (PD1) and sixth photodiode (PD5) photodiode is measured.

In one example voltage configuration to implement an example of the "relative" measurement mode, the voltage levels of the voltage nodes are set as follows (where "Vm" is the measurement voltage, i.e. a node at which the current measurement is taken; Vbn is a first bias voltage which is the voltage to apply to a photodiode anode to hold it in a reverse bias state "relative" to Vm; Vbp is a second bias voltage which is the voltage to apply to a photodiode cathode to hold it in a reverse bias state "relative" to Vm. Vbx is a null voltage, where a photodiode is held in an unbiased state.

Typically, Vbn<Vm<Vbp.

Figure 5A:
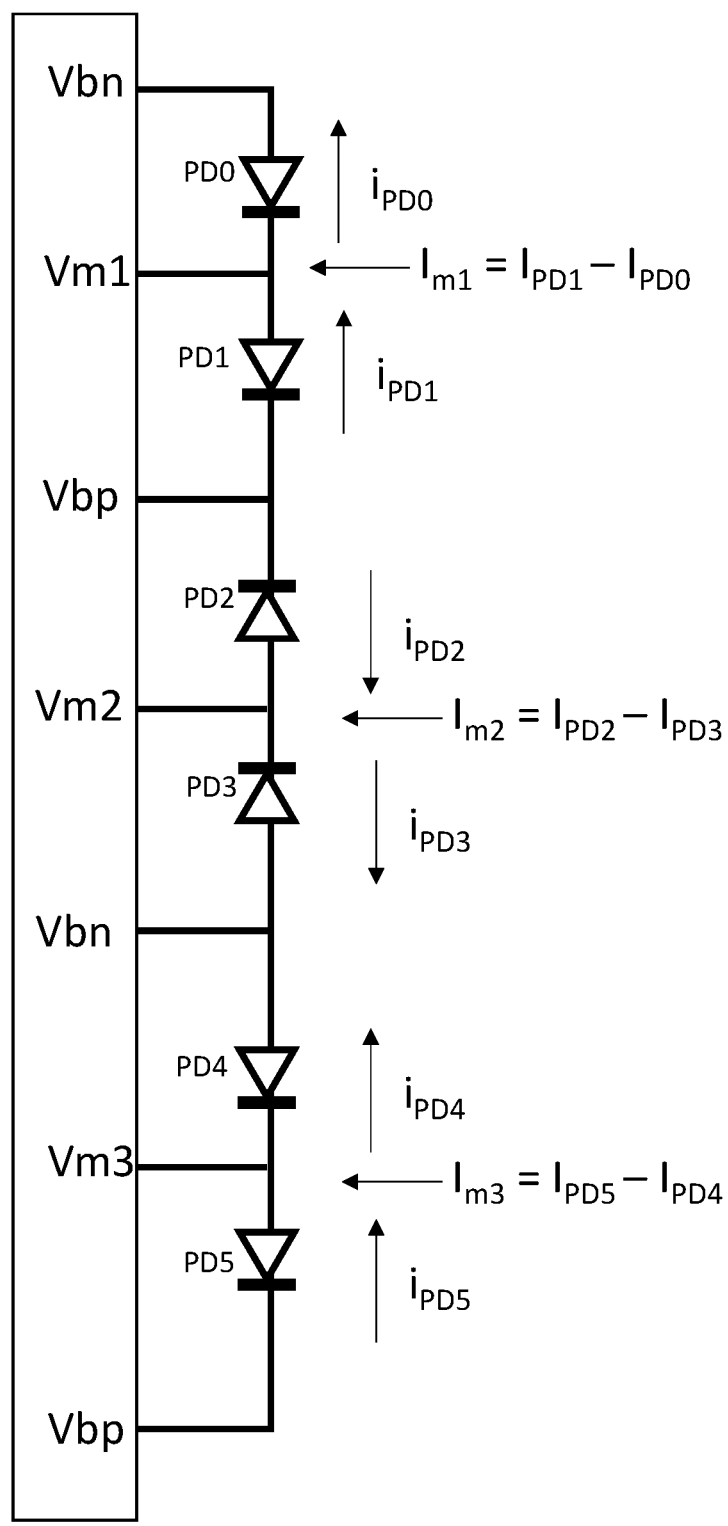
FIG. 5a provides a schematic diagram depicting configuration of a photodiode array for implementing a "relative" measurement mode in accordance with certain embodiments of the invention.

Typically, Vm<Vbx<Vm+Vf (where Vf is the forward voltage of the photodiode):

As can be seen from FIG. 5a, V0=Vbn; V1=Vm1; V2=Vbp; V3=Vm2; V4=Vbn; V5=Vm3; and V6=Vbp.

This is shown in FIG. 5a. Specifically, FIG. 5a depicts a voltage configuration which when applied to a photodiode array of the type described with reference to FIG. 4, implements an example of the "relative" measurement mode.

As can be seen from FIG. 5a, by virtue of this application of bias voltages, the first photodiode PD0 and the second photodiode PD1 are held in a reverse bias state by virtue of the third voltage node being held at Vbp and the first voltage node being held at Vbn.

As a result, the net current $I_{m1}$ at the second voltage node (Vm1) is the current flowing through the second photodiode PD1 $i_{PD1}$ less the current flowing through the first photodiode PD0 $i_{PD0}$.

Similarly, the fourth photodiode PD3 and the third photodiode PD2 are held in a reverse bias state by virtue of the third voltage node being held at Vbp and the fifth voltage node being held at Vbn. As a result, the net current $I_{m2}$ at the fourth voltage node (Vm2) is the current flowing through the third photodiode PD2 $i_{PD2}$ less the current flowing through the fourth photodiode PD3 $i_{PD3}$.

Similarly, the fifth photodiode PD4 and the sixth photodiode PD5 are held in a reverse bias state by virtue of the seventh voltage node being held at Vbp and the fifth voltage node being held at Vbn. As a result, the net current $I_{m3}$ at the sixth voltage node (Vm3) is the current flowing through the sixth photodiode PD5 $i_{PD5}$ less the current flowing through the fifth photodiode PD4 $i_{PD4}$.

In one example, to implement the "absolute" measurement mode in the photodiode array configuration described with reference to FIG. 4, two voltage configurations are used. In the first voltage configuration, the incident light detected by a first half of the photodiodes is measured, and in the second voltage configuration, the incident light detected by the second half of the photodiodes is measured. Typically, therefore, when measuring the incident light in the "absolute" measurement mode in this way, the first voltage configuration is used, followed by the second voltage configuration.

In a first of these voltage configurations, the voltage levels of the voltage nodes are set as follows (where Vbx is a null voltage in which a photodiode is held in an unbiased state):
V0=Vbx; V1=Vm1; V2=Vbp; V3=Vm2; V4=Vbx; V5=Vm3; and V6=Vbp.

Figure 5B:
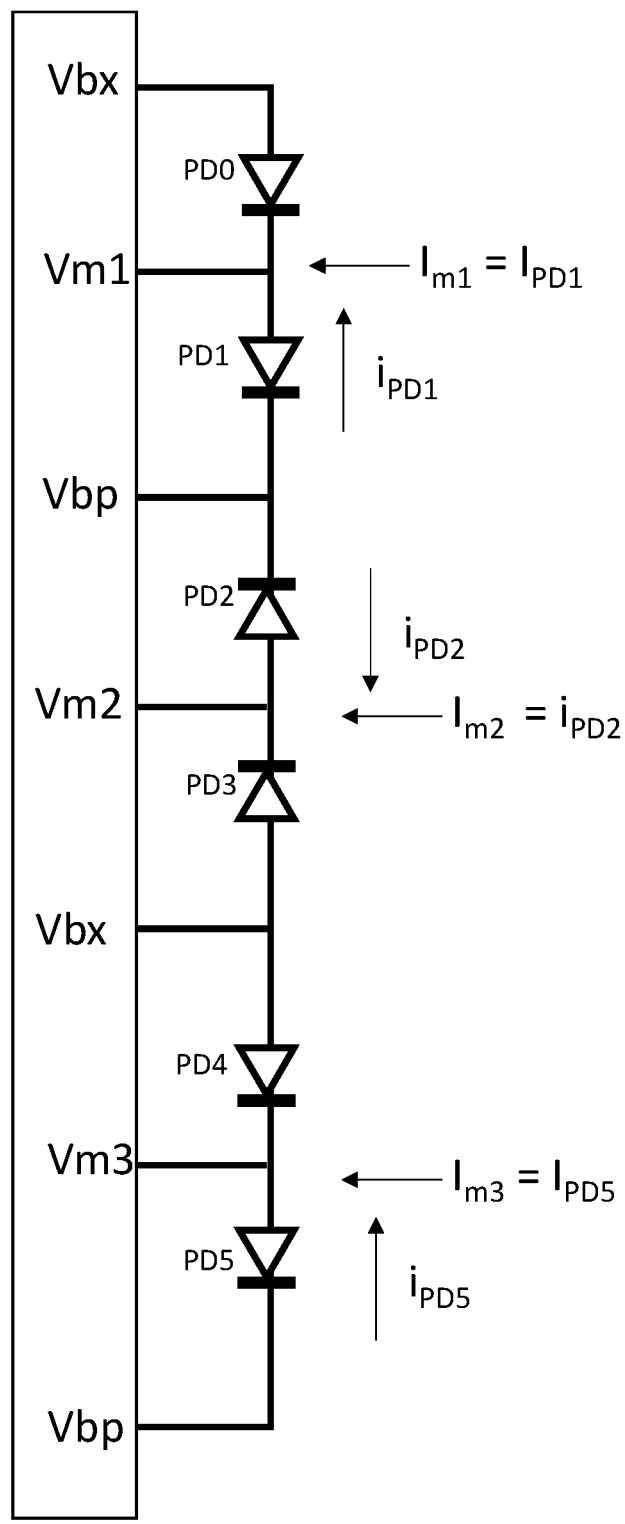
FIG. 5b provides a schematic diagram depicting configuration of a photodiode array for implementing a first "absolute" measurement mode in accordance with certain embodiments of the invention.

The operation of this first voltage configuration is shown in FIG. 5b.

As can be seen from FIG. 5b, by virtue of this application of bias voltages, the first photodiode PD0 is held in an unbiased state by virtue of the application of the null voltage on the first voltage node and thus it can be approximated that no current is generated. However, as the third voltage node is held at Vbp, the second photodiode PD1 is held in a reverse bias state. Therefore, the current $I_{m1}$ at the second voltage node Vm1 is the current flowing through second photodiode PD1.

Similarly, the fourth photodiode PD3 is held in an unbiased state by virtue of the application of the null voltage on the fifth voltage node and thus it can be approximated that no current is generated. However, as the third voltage node is held at Vbp, the third photodiode PD2 is held in a reverse bias state. Therefore, the current $I_{m2}$ at the fourth voltage node Vm2 is the current $i_{PD2}$ flowing through third photodiode PD2.

Similarly, the fifth photodiode PD4 is held in an unbiased state by virtue of the application of the null voltage on the fifth voltage node and thus it can be approximated that no current is generated. However, as the seventh voltage node is held at Vbp, the sixth photodiode PD5 is held in a reverse bias state. Therefore, the current $I_{m3}$ at the sixth voltage node Vm3 is the current $i_{PD5}$ flowing through sixth photodiode PD5. The current flowing through the sixth photodiode PD5

In a second of these voltage configurations, the voltage levels of the voltage nodes are set as follows:
V0=Vbn; V1=Vm1; V2=Vbx; V3=Vm2; V4=Vbn; V5=Vm3; and V6=Vbx.

Figure 5C:
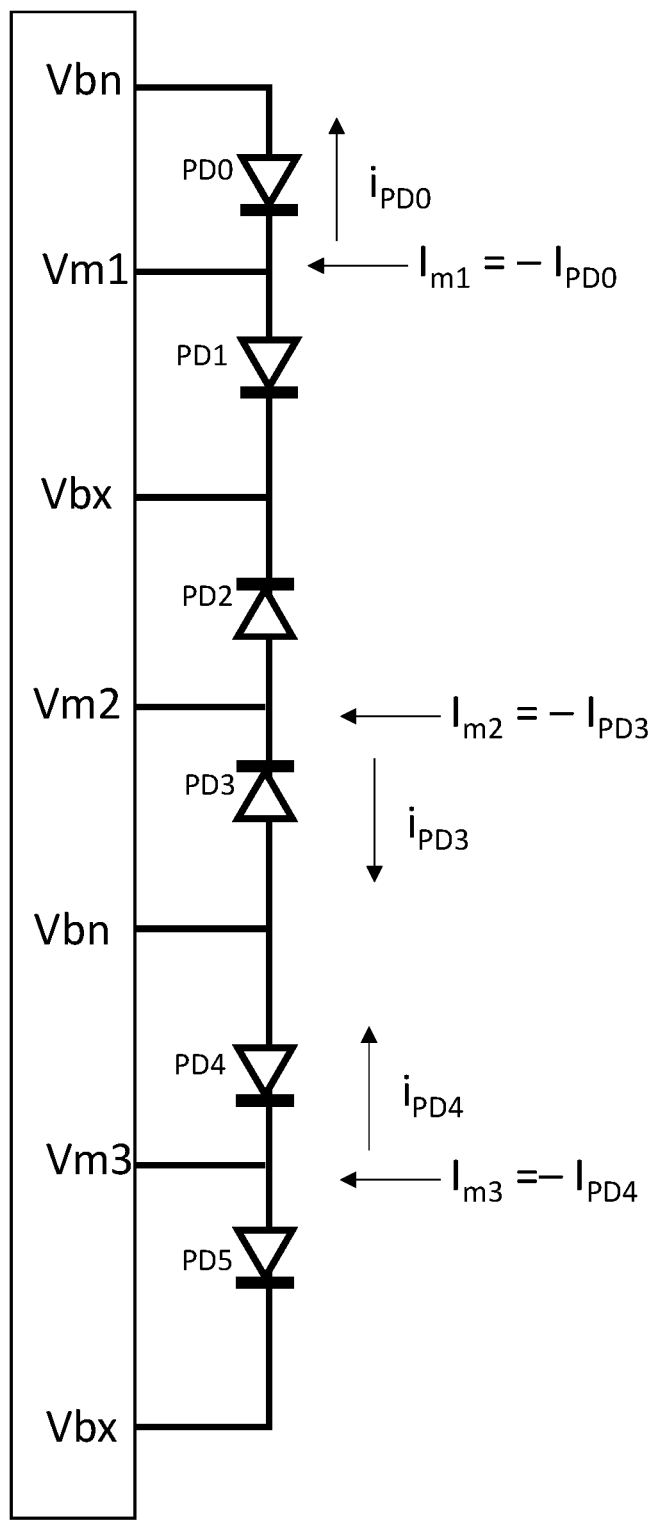
FIG. 5c provides a schematic diagram depicting configuration of a photodiode array for implementing a second "absolute" measurement mode in accordance with certain embodiments of the invention.

The operation of this second voltage configuration is shown in FIG. 5c.

As can be seen from FIG. 5c, by virtue of this application of bias voltages, the second photodiode PD1 is held in an unbiased state by virtue of the application of the null voltage on the third voltage node and thus it can be approximated that no current is generated. However, as the first voltage node is held at Vbn, the first photodiode PD0 is held in a reverse bias state. Therefore, the current $I_{m1}$ at the second voltage node Vm1 is the current flowing through second photodiode PD1 (note the current flows from the second voltage node Vm1).

Similarly, the third photodiode PD2 is held in an unbiased state by virtue of the application of the null voltage on the third voltage node and thus it can be approximated that no current is generated. However, as the fifth voltage node is held at Vbn, the fourth photodiode PD3 is held in a reverse bias state. Therefore, the current $I_{m2}$ at the fourth voltage node Vm2 is the current $i_{PD3}$ flowing through the fourth photodiode PD3 (note the current flows from the fourth voltage node Vm2). The current flowing through the fourth photodiode PD3

Similarly, the sixth photodiode PD5 is held in an unbiased state by virtue of the application of the null voltage on the seventh voltage node and thus it can be approximated that no current is generated. However, as the fifth voltage node is held at Vbn, the fifth photodiode PD4 is held in a reverse bias state. Therefore, the current $I_{m3}$ at the sixth voltage node Vm2 is the current $i_{PD4}$ flowing through the fifth photodiode PD4 (note the current flows from the sixth voltage node Vm3). The current flowing through the fifth photodiode PD4

Figure 5D:
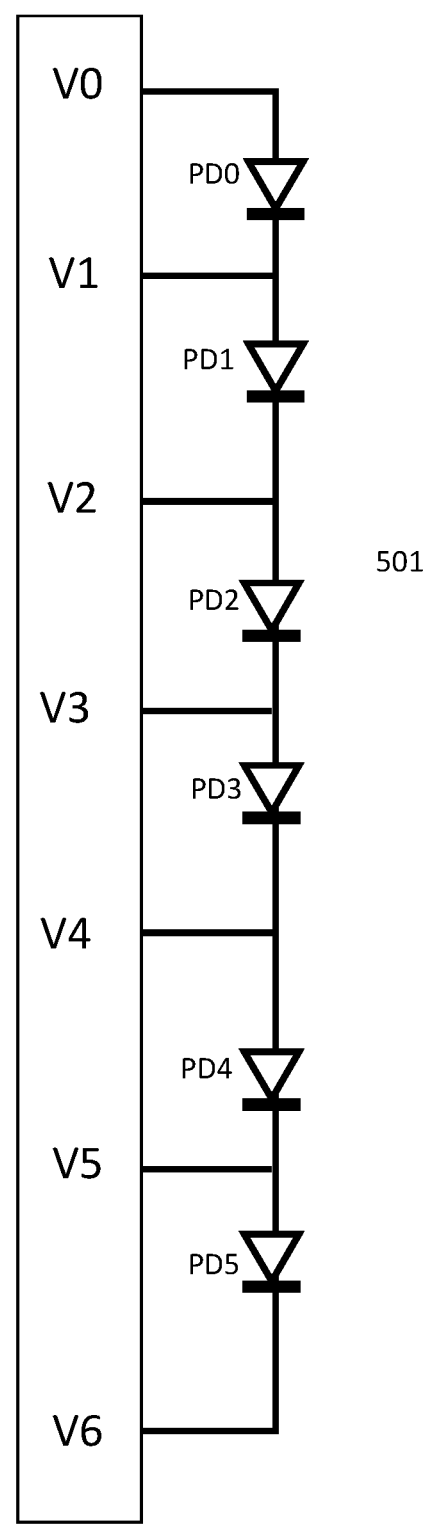
FIG. 5d provides a schematic diagram of a depicting a photodiode array in accordance with certain embodiments of the invention.

In the examples shown in FIGS. 5a to 5c, the array of photodiodes is divided into photodiode pairs and the photodiode pairs are arranged with alternating polarity. In certain embodiments, the array of photodiodes is arranged so that the photodiodes are arranged in series with the same polarity. An example of such an arrangement in FIG. 5d. Specifically, FIG. 5d depicts the physical configuration of a photodiode array 501 in which the photodiodes are connected in series with the same polarity.

In keeping with the photodiode array 401 described with reference to FIG. 4, the photodiode array 501 shown in FIG. 5 comprises seven voltage nodes that can be controlled: a first voltage node V0 at the anode of the first photodiode PD0; a second voltage node V1 at the cathode of the first photodiode PD0 and the anode of the second photodiode PD1; a third voltage node V2 at the cathode of the second photodiode PD1 and the anode of the third photodiode PD2; a fourth voltage node V3 at the cathode of the third photodiode PD2 and the anode of the fourth photodiode PD3; a fifth voltage node V4 at the cathode of the fourth photodiode PD3 and the anode of the fifth photodiode PD4; a sixth voltage node V5 at the cathode of the fifth photodiode PD4 and the anode of the sixth photodiode PD5, and a seventh voltage node V6 at the cathode of the sixth photodiode PD5.

In a first example, this arrangement can be configured in a "relative" measurement mode in which a voltage configuration is applied such that each voltage node is held at 0V. The operation of this voltage configuration is shown in FIG. 5e.

In this configuration V0=0V; V1=0V; V2=0V; V3=0V; V4=0V; V5=0V; and V6=0V.

Figure 5E:
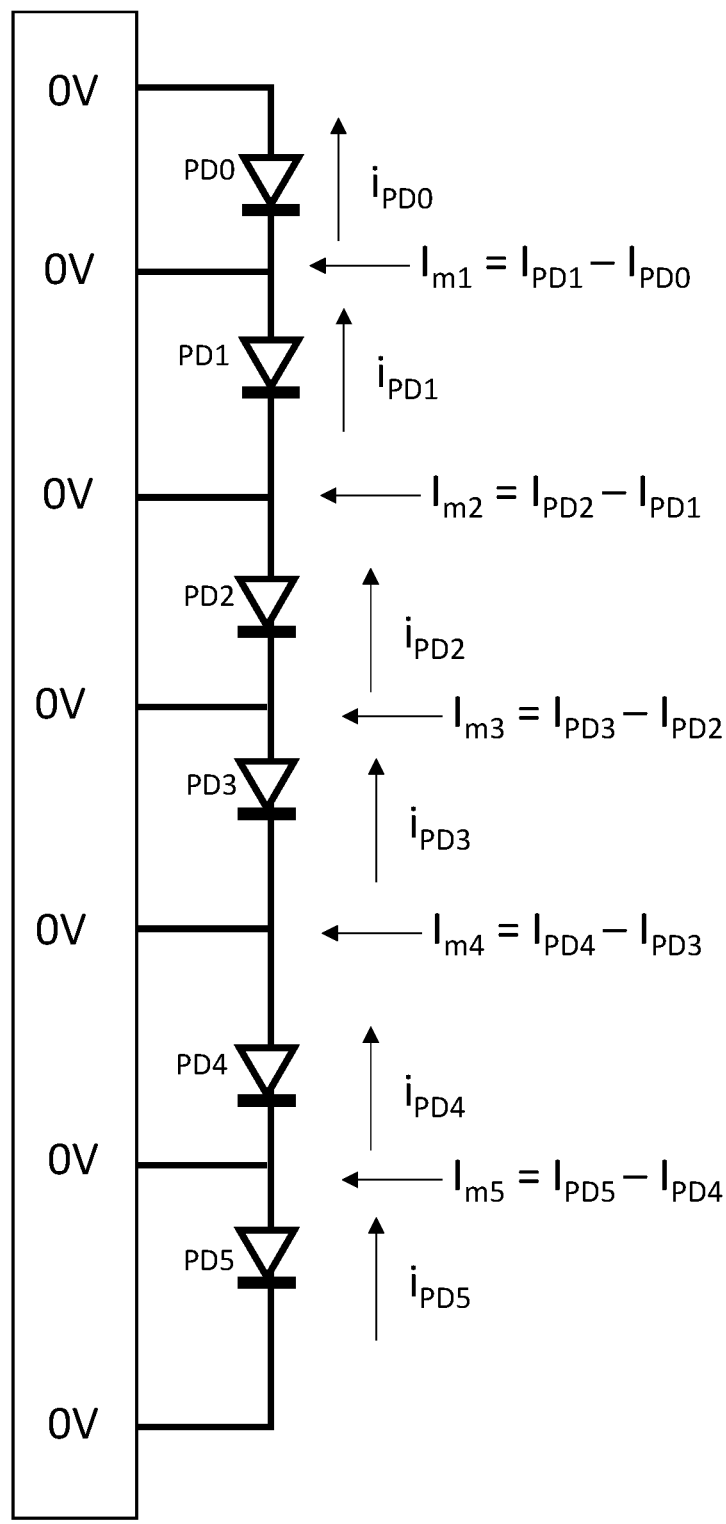
FIG. 5e provides a schematic diagram depicting configuration of a photodiode array for implementing a further "relative" measurement mode in accordance with certain embodiments of the invention.

As can be seen from FIG. 5e, by virtue of this configuration the current $I_{m1}$ at the second voltage node Vm1 is the difference between the current flowing through the second photodiode $I_{PD1}$ and the first photodiode $I_{PD0}$; the current $I_{m2}$ at the third voltage node Vm2 is the difference between the current flowing through the third photodiode $I_{PD2}$ and the second photodiode $I_{PD1}$; the current $I_{m3}$ at the fourth voltage node Vm3 is the difference between the current flowing through the fourth photodiode $I_{PD3}$ and the third photodiode $I_{PD2}$; the current $I_{m4}$ at the fifth voltage node Vm4 is the difference between the current flowing through the fifth photodiode $I_{PD4}$ and the fourth photodiode $I_{PD3}$, and the current $I_{m5}$ at the sixth voltage node Vm5 is the difference between the current flowing through the sixth photodiode $I_{PD5}$ and the fifth photodiode $I_{PD4}$.

Figure 5F:
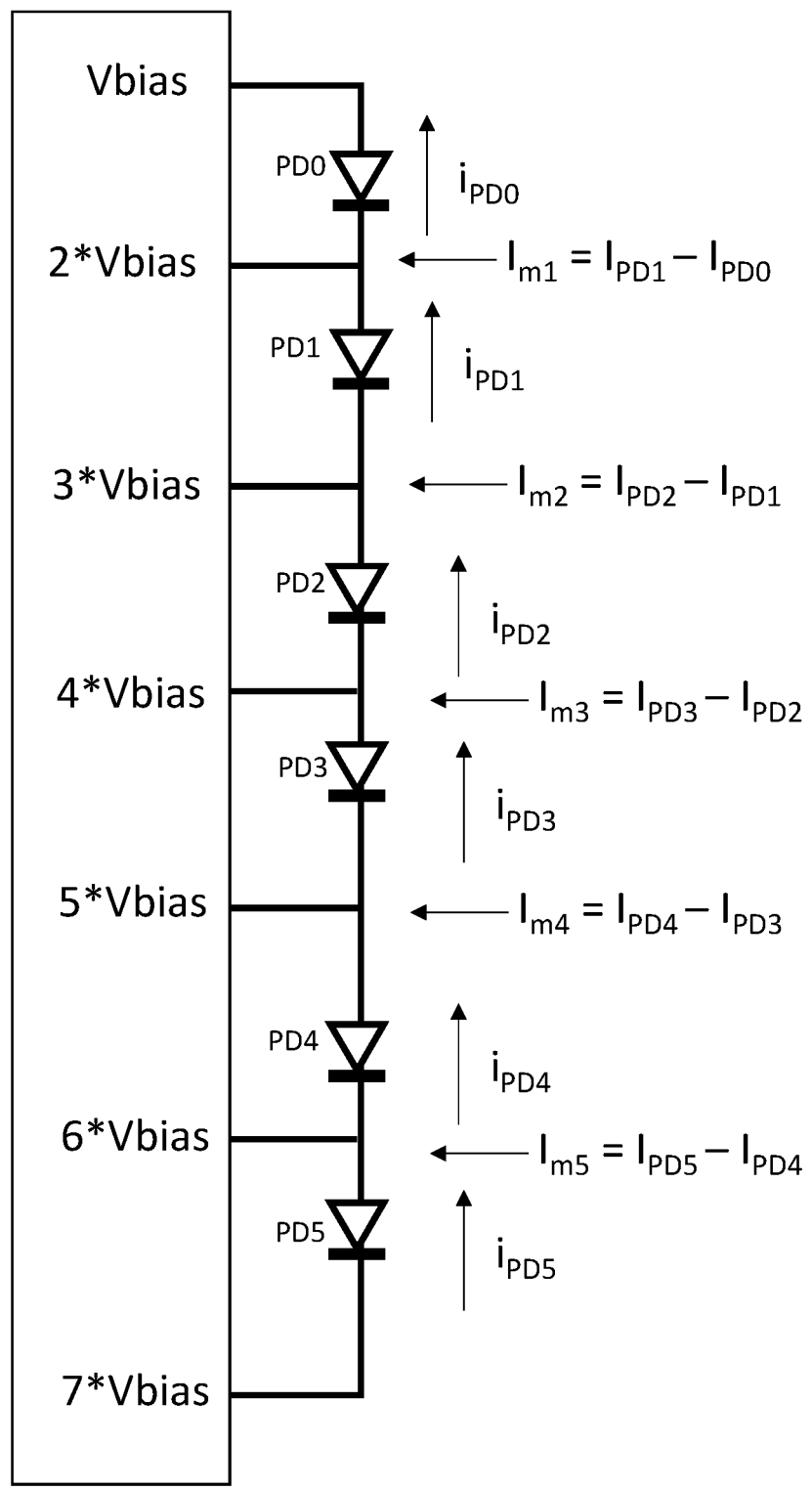
FIG. 5f provides a schematic diagram depicting a further "relative" measurement configuration of a photodiode array in accordance with certain embodiments of the invention.

In another configuration, a voltage configuration is applied that implements a "relative" measurement mode in a different way. In this voltage configuration, each voltage node is held at a sequentially higher voltage ensuring that each photodiode is held in a reverse biased state. The operation of this voltage configuration is shown in FIG. 5f.

In this configuration V0=Vbias; V1=2*Vbias; V2=3*Vbias; V3=4*Vbias; V4=5*Vbias; V5=6*Vbias; and V6=7*Vbias.

By virtue of this configuration, the current $I_{m1}$ at the second voltage node (held at 2*Vbias) is the difference between the current flowing through the second photodiode $I_{PD1}$ and the first photodiode $I_{PD0}$; the current $I_{m2}$ at the third voltage node (held at 3*Vbias) is the difference between the current flowing through the third photodiode $I_{PD2}$ and the second photodiode $I_{PD1}$; the current $I_{m3}$ at the fourth voltage node (held at 4*Vbias) is the difference between the current flowing through the fourth photodiode $I_{PD3}$ and the third photodiode $I_{PD2}$; the current $I_{m4}$ at the fifth voltage node (held at 5*Vbias) is the difference between the current flowing through the fifth photodiode $I_{PD4}$ and the fourth photodiode $I_{PD3}$, and the current $I_{m5}$ at the sixth voltage node (held at 6*Vbias) is the difference between the current flowing through the sixth photodiode $I_{PD5}$ and the fifth photodiode $I_{PD4}$.

As will be understood, for both the configuration shown in FIG. 5e and the configuration shown in 5f, "relative" measurements are provided for pairs of photodiodes formed of the first photodiode PD0 and the second photodiode PD1; second photodiode PD1 and the third photodiode PD2; third photodiode PD2 and the fourth photodiode PD3; fourth photodiode PD3 and the fifth photodiode PD4, and the fifth photodiode PD4 and the sixth photodiode PD5.

In certain implementations, where the number of voltage levels available is limited, the "relative" measurement mode is provided by applying a voltage configuration in which the photodiodes can be divided into "batches". As described below, this requires an adaptation to the physical configuration of the photodiode array.

Figure 5G:
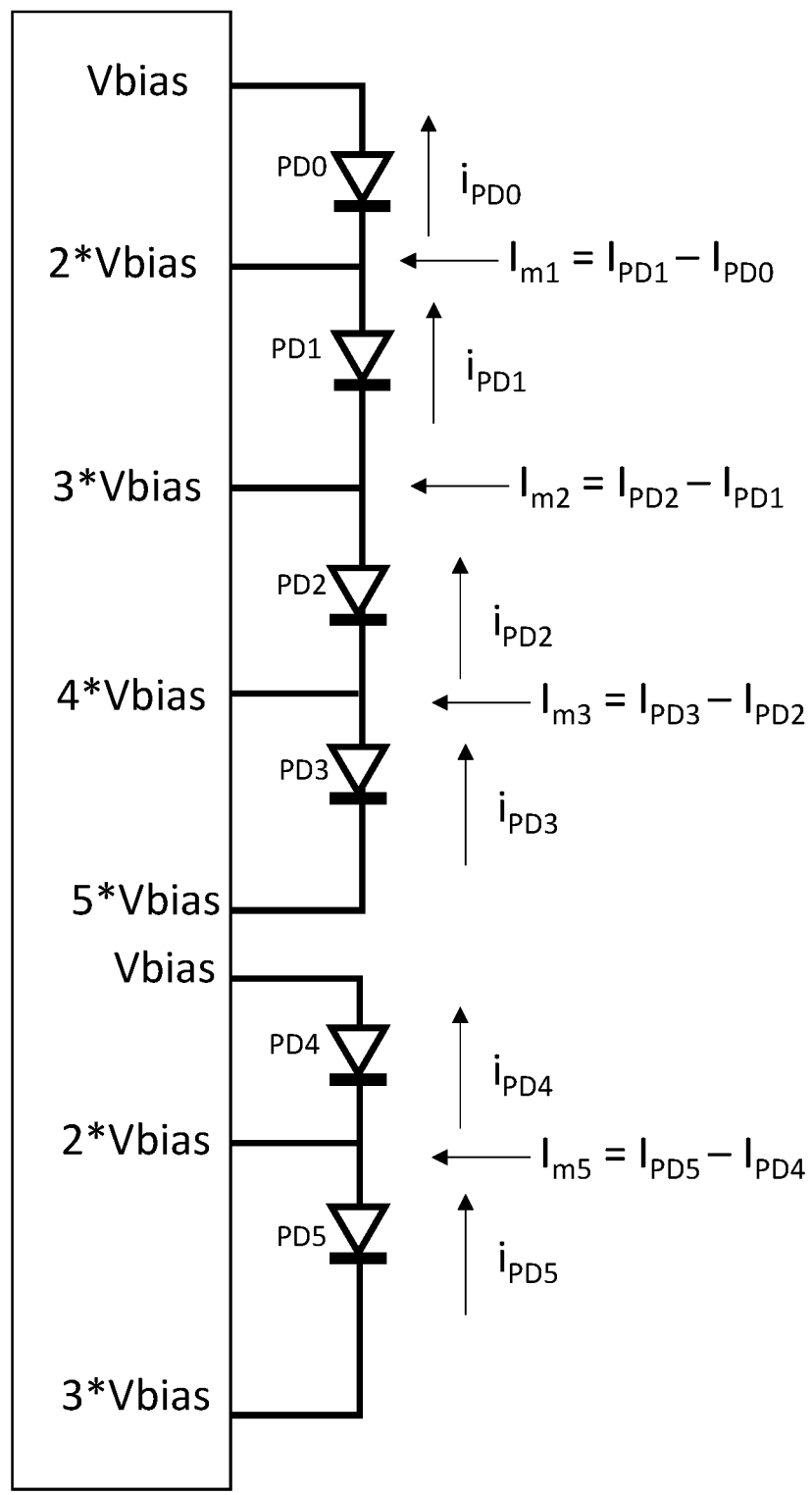
FIG. 5g provides a schematic diagram depicting configuration of a photodiode array for implementing a further "relative" measurement mode in accordance with certain embodiments of the invention.

FIG. 5g provides a diagram depicting the application of this voltage configuration where the number of available voltage levels is restricted to four bias voltage levels and depicts the adaptation to the photodiode array.

In this configuration, V0=Vbias; V1=2*Vbias; V2=3*Vbias; V3=4*Vbias; V4=5*Vbias; V5=Vbias; V6=2*Vbias, and V7=3*Vbias.

By virtue of this configuration, the current $I_{m1}$ at the second voltage node (held at 2*Vbias) is the difference between the current flowing through the second photodiode $I_{PD1}$ and the first photodiode $I_{PD0}$; the current $I_{m2}$ at the third voltage node (held at 3*Vbias) is the difference between the current flowing through the third photodiode $I_{PD2}$ and the second photodiode $I_{PD1}$; the current $I_{m3}$ at the fourth voltage node (held at 4*Vbias) is the difference between the current flowing through the fourth photodiode $I_{PD3}$ and the third photodiode $I_{PD2}$.

At the fifth voltage node, the physical arrangement of the photodiode is array is adapted. Specifically, typically the connection between the cathode of the fourth photodiode PD3 and the anode of the fifth photodiode PD4 is broken (for example by a switch, not shown) to protect the fifth photodiode PD4 from large forward currents.

No measurement current is collected at the fifth voltage node.

The current $I_{m5}$ at the seventh voltage node (held at 2*Vbias) is the difference between the current flowing through the sixth photodiode $I_{PD5}$ and the fifth photodiode $I_{PD4}$.

In keeping with the embodiments described above with reference to FIGS. 5a, 5b and 5c for photodiode arrays in which the polarity of photodiode pairs alternates, in embodiments in which the photodiode array is arranged with all the photodiodes connected in series and with the same polarity, to implement the "absolute" measurement mode, two voltage configurations are used. In the first voltage configuration, the incident light detected by a first half of the photodiodes is measured, and in the second voltage configuration, the incident light detected by the second half of the photodiodes is measured. Typically, therefore, when measuring the incident light in the "absolute" measurement mode in this way, the first voltage configuration is used, followed by the second voltage configuration.

Figure 5H:
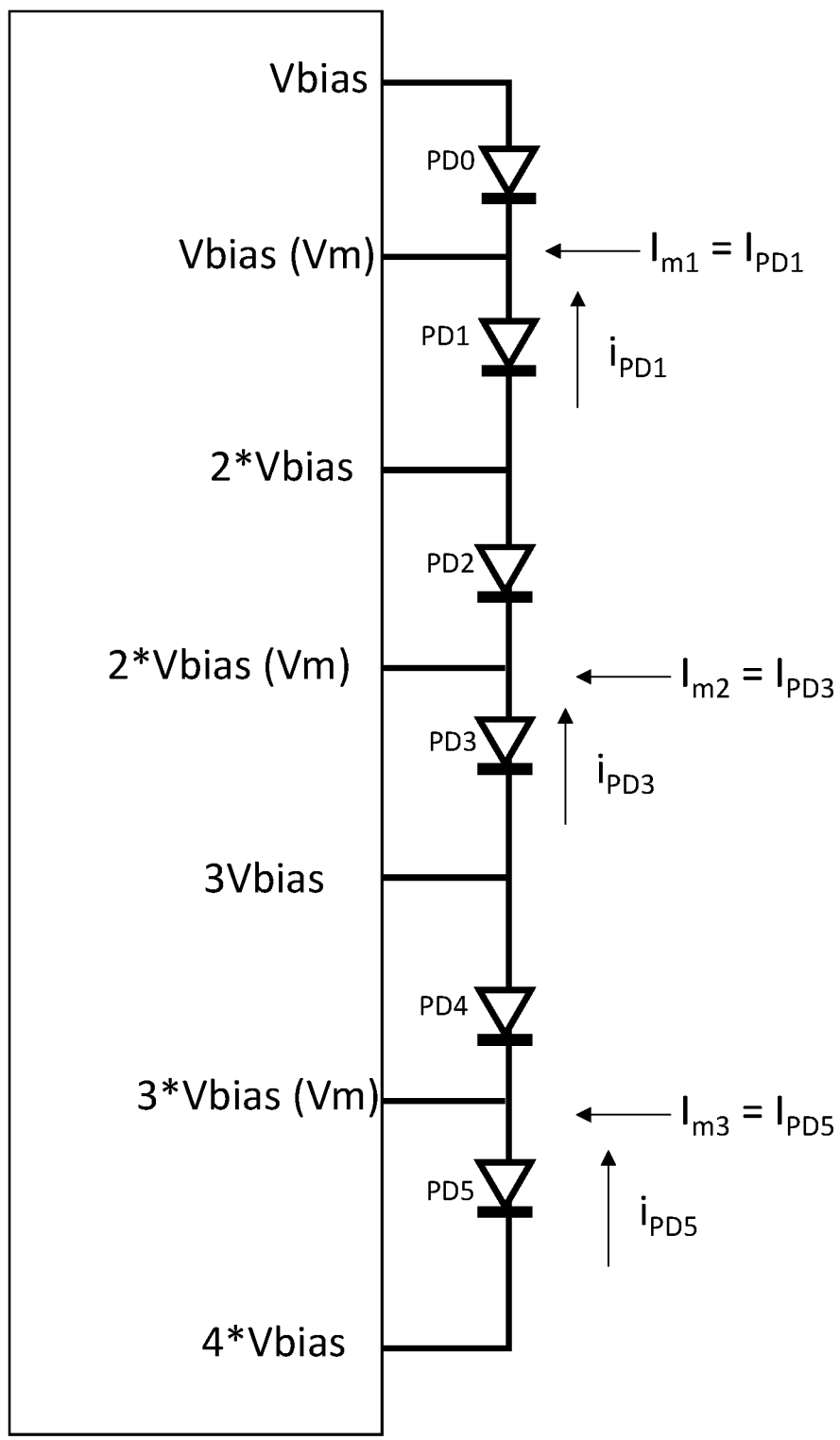
FIG. 5h provides a schematic diagram depicting configuration of a photodiode array for implementing a first "absolute" measurement mode in accordance with certain embodiments of the invention.

FIG. 5h provides a diagram of the implementation of such an "absolute" measurement mode by initially applying a first voltage configuration. In this voltage configuration the voltage levels of the voltage nodes are set as follows:

In this voltage configuration V0=Vbias; V1=Vbias (Vm); V2=2*Vbias; V3=2*Vbias (Vm); V4=3*Vbias; V5=3*Vbias (Vm); and V6=4*bias. Note Vbias=Vbias (Vm), 2*Vbias=2*Vbias (Vm) and 3Vbias=3*Vbias (Vm). Note Vbias=Vbias (Vm), 2*Vbias=2*Vbias (Vm) and 3*Vbias=3*Vbias (Vm).

By virtue of this voltage configuration, the current $I_{m1}$ at the second voltage node (Vbias (Vm)) is the current through the second photodiode PD1 because the first photodiode PD0 is held in the unbiased state, it can be approximated that no current is generated by the first photodiode PD0.

Further, the current $I_{m2}$ at the fourth voltage node (2*Vbias (Vm)) is the current through the fourth photodiode PD3 because the third photodiode PD2 is held in the unbiased state, it can be approximated that no current is generated by the third photodiode PD2.

Figure 5I:
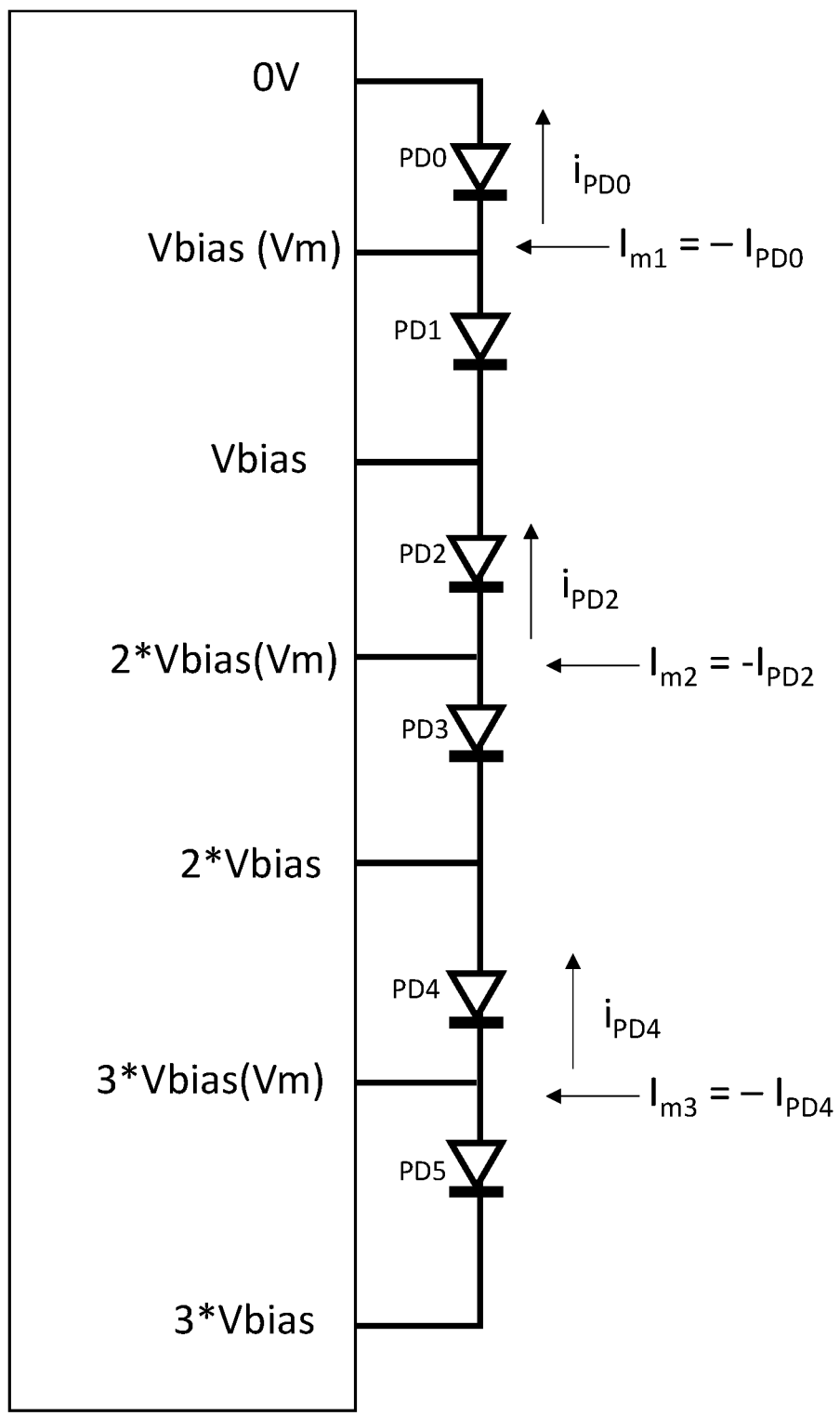
FIG. 5i provides a schematic diagram depicting configuration of a photodiode array for implementing a first "absolute" measurement mode in accordance with certain embodiments of the invention.

Similarly, the current $I_{m3}$ at the sixth voltage node (3*Vbias (Vm)) is the current through the sixth photodiode PD5, because the fifth photodiode PD4 is held in the unbiased state, it can be approximated that no current is generated by the fifth photodiode PD4. FIG. 5i provides a diagram of the implementation of the "absolute" measurement mode by subsequently applying a second voltage configuration. In this voltage configuration the voltage levels of the voltage nodes are set as follows:

V0=0V; V1=Vbias (Vm); V2=Vbias; V3=2*Vbias (Vm); V4=2*Vbias; V5=3*Vbias (Vm); and V6=3*Vbias. Note, again, Vbias=Vbias (Vm), 2*Vbias=2*Vbias (Vm) and 3*Vbias=3*Vbias (Vm).

By virtue of this configuration, the current $I_{m1}$ at the second voltage node (Vm1) is the current through the first photodiode PD0, because the second photodiode PD1 is held in the unbiased state, it can be approximated that no current is generated by the second photodiode PD1.

Further, the current $I_{m2}$ at the fourth voltage node (Vm2) is the current through the third photodiode PD2, because the fourth photodiode PD3 is held in the unbiased state, it can be approximated that no current is generated by the fourth photodiode PD3.

Similarly, the current $I_{m3}$ at the sixth voltage node (Vm3) is the current through the fifth photodiode PD4, because the sixth photodiode PD5 is held in the unbiased state, it can be approximated that no current is generated by the sixth photodiode PD5.

In the example voltage configurations described above in which the voltage nodes are set so that the photodiode array is in an "absolute" measurement mode (i.e. the voltage configurations depicted with reference to FIGS. 5b, 5c, 5h and 5i) the current flowing through the non-biased photodiodes—i.e. those connected (either via anode or cathode) to the null voltage "Vbx" is shown as zero. This is because in the non-biased state they have a much greater time constant than the photodiodes in the biased configuration and therefore can be considered to effectively contribute a zero current. For this reason, in most implementations they can effectively be considered to contribute zero current.

However, in such voltage configurations, photodiodes in the non-biased state will gives rise to a small current. This can be considered to be the current that would normally be stimulated if the photodiode was in the reverse bias state multiplied by an attenuation factor. Ideally, the attenuation factor is zero (and, as described above, this is the assumption made in 5b, 5c, 5h and 5i). However, typically the attenuation is non-zero. The magnitude of the attenuation factor is governed by the frequency of the incident light. Typical frequencies of incident light are selected so that the attenuation factor is as close to zero as possible. For example, the typical frequency operation range is between 10 kHz and 10 MHz In certain embodiments, to implement the different measurement modes, the voltage nodes of the photodiode array can be connected to the relevant voltage levels and outputs via a switching matrix.

Figure 6:
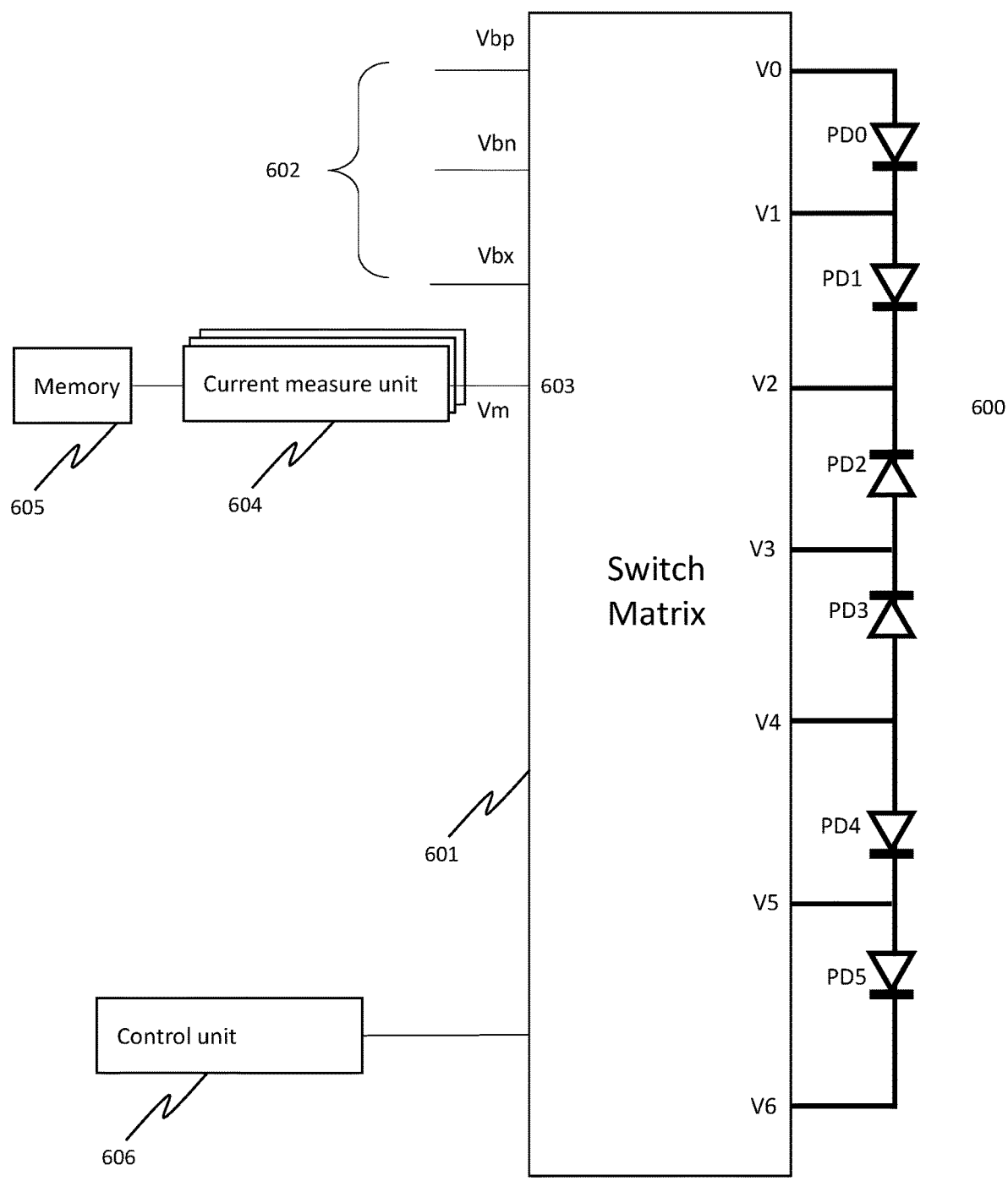
FIG. 6 provides a schematic diagram of a light detection unit in accordance with certain embodiments of the invention.

An example of this is depicted schematically in FIG. 6. FIG. 6 provides a schematic diagram of a light detection unit in accordance with certain embodiments of the invention.

The example depicted in FIG. 6 shows the arrangement for a photodiode array in which photodiode pairs are arranged with alternating polarities (corresponding with the example voltage configurations described with reference to FIGS. 5a to 5c).

However, it will be understood that the arrangement also works for photodiode arrays in which the photodiodes are arranged in series with the same polarity as depicted, for example, in FIGS. 5d to 5i. The skilled person will understand that the photodiode array 601 is simply replaced with a photodiode array physically configured as shown, for example, in FIG. 5d.

In FIG. 6, a switching matrix 601 is connected to the photodiode array 600.

In operation, under the control of a control unit 606 the switching matrix 601 connects the relevant voltage nodes of the photodiode array 600 to suitable voltage level input lines 602 and an output 603 line held at $V_m$.

In the example shown in FIG. 6, the voltage input lines provide a first voltage line at Vbp, a second voltage line at Vbn and a third voltage line at Vbx. The switching matrix 601 can therefore implement the voltage configurations described with reference to FIGS. 5a, 5b and 5c. However, it will be understood that in embodiments implementing other voltage configurations, the requisite voltages required at each node are provided by a corresponding number of voltage input lines providing the requisite voltages. For example, for voltage configurations such as those described with reference to FIG. 5f, multiple voltage input lines will be provided corresponding to Vbias, 2*Vbias, 3*Vbias, 4*Vbias, 5*Vbias, 6*Vbias, 7*Vbias (and so on depending on the number of photodiodes in the photodiode array).

Further, in operation, under the control of the control unit 606 the switching matrix 601 connects the relevant voltage node of the photodiode array to the output 603. The output 603 is connected to a current measurement unit 604 which converts the output to a digital value which is then stored in a memory unit 605. Together, the switching matrix 601 and the current measurement unit 604 form the measurement processing unit described with reference to FIG. 2.

The current measurement unit 604 can be provided by any suitable means for measuring current. The current measurement unit may be provided by an arrangement that passes the generated current across a resistance and the corresponding voltage that is produced is measured. Measuring a voltage in this manner means that the voltage can be sampled continuously during the measurement cycle. Other means of measuring the current include the use of op-amps as is known in the art.

In certain examples, the current measurement unit 604 may be provided by a charge collector performing a sampling operation. A single current measurement unit can used or, in other implementations, multiple current measurement units may be provided allowing multiple current measurements to be performed in parallel.

During a measurement cycle in the "relative" measurement mode, the voltage nodes are held at the required voltage level and the current from the output 603 for each photodiode pair is measured. This is achieved by the switching matrix 601 sequentially connecting the relevant voltage nodes (V1, V3 and V5 in the example shown in FIG. 6) to the output 603 and thus the current measure unit 604. The current measurement unit 604 then converts the current measurement (for example amount of collected charge or sampled voltage level) into a digital value (using, for example, a conventional analogue to digital convertor). The digital value for each current measure this is then communicated to the memory 605 for onward communication to the image processing module 109.

During a measurement cycle in the "absolute" measurement mode, the voltage nodes are held at the required voltage level and the current from the output 603 for each photodiode is measured. Similarly, this is achieved by the switching matrix 601 sequentially connecting the relevant voltage nodes to the output 603 and thus the current measurement unit 604. The current measurement unit 604 then converts the current measurement to a digital value for onward communication to the image processing module 109 as described above.

The measurement processing unit can be implemented in any suitable way. In certain examples, it may be integrated onto a single silicon device.

In the embodiments described above, the measurement modes are selected by applying the requisite voltage to the requisite voltage nodes. This means that the photodiodes of the photodiode array can simply be connected directly to one another in series which can, in certain examples, simplify the layout of the photodiode array.

However, in certain examples, the photodiodes of the photodiode array are not directly connected to one another in series but are instead connected in series via a plurality of physical switches.

Figure 7A:
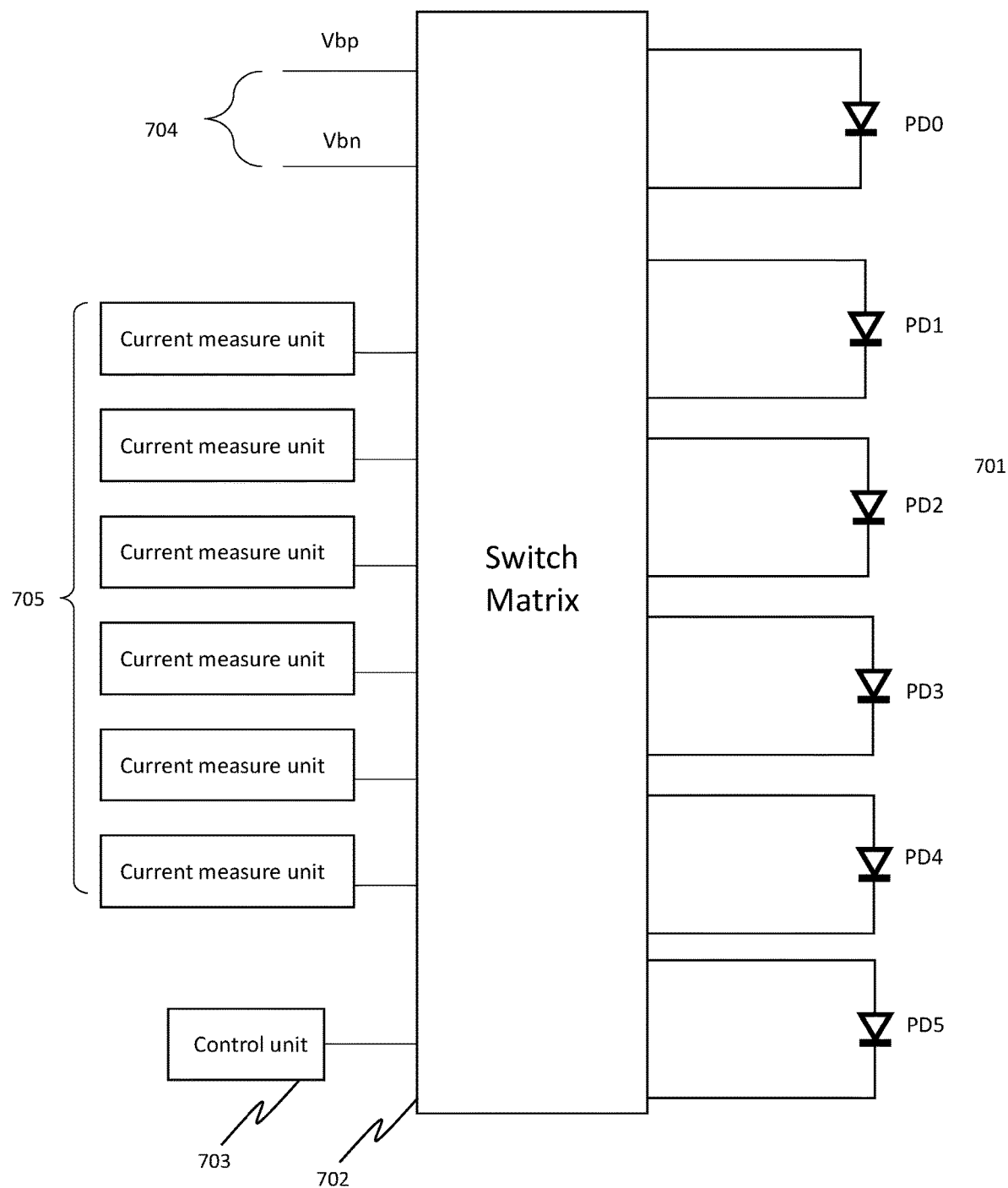
FIG. 7a provides a schematic diagram of a light detection unit in accordance with certain embodiments of the invention, in which the light detectors of the light detector array are individually connected to input lines of a switching matrix.

FIG. 7a provides a schematic diagram of another embodiment in which the measurement modes are implemented by a physical switching arrangement.

FIG. 7a corresponds to the arrangement shown in FIG. 6 except that a photodiode array 701 is provided in which the anode and cathode of each individual photodiode is connected directly to input lines of a switching matrix 702. Under the control of a control unit 703, the switching matrix is arranged to connect the photodiode anodes and cathodes to voltage input lines 704, and to a plurality of current measurement units 705 to implement the different measurement modes.

Figure 7B:
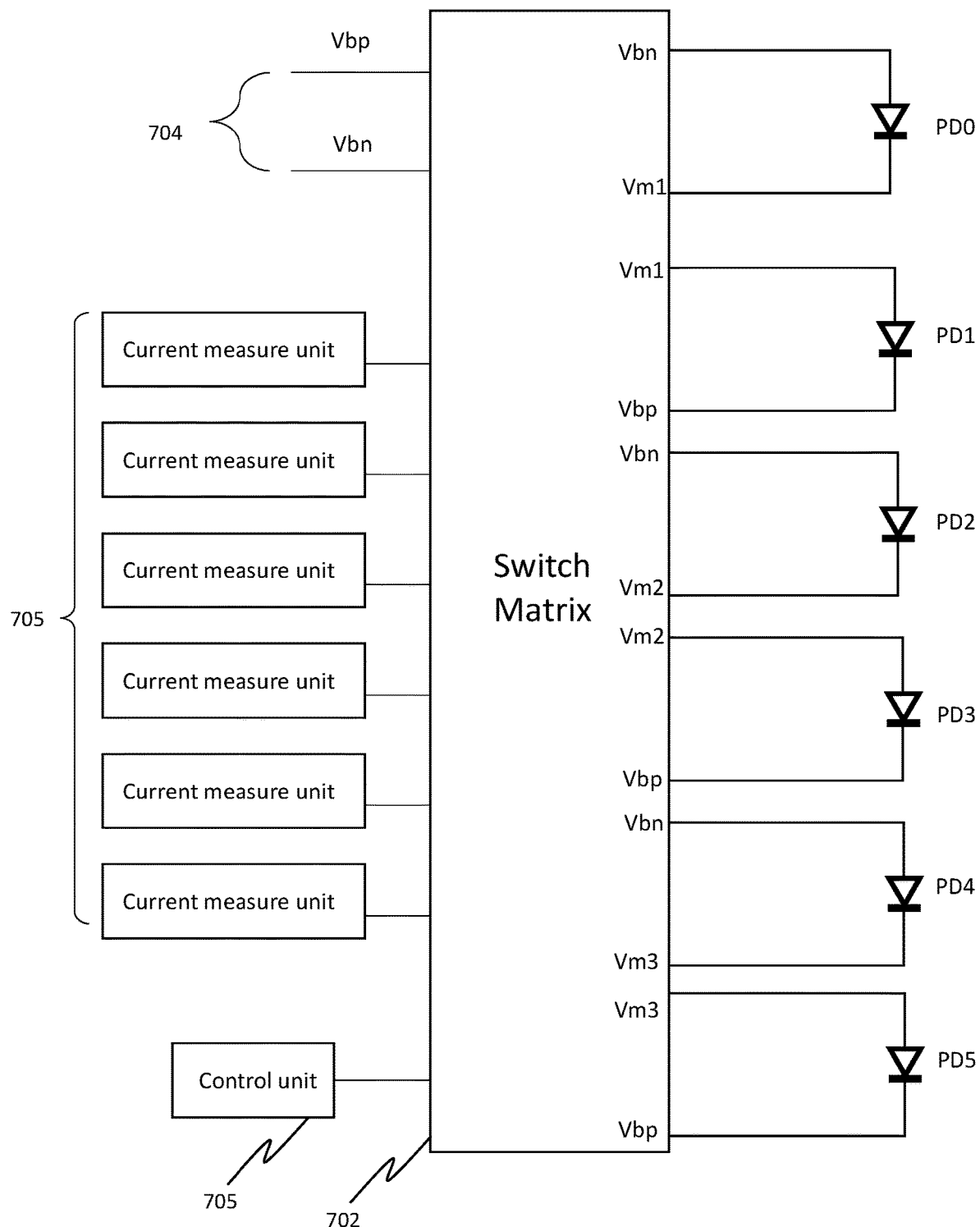
FIG. 7b provides a schematic diagram depicting configuration of the light detection unit shown in FIG. 7a to provide a "relative" measurement mode.

FIG. 7b provides a schematic diagram showing the voltage connections necessary to implement a first "relative" measurement configuration in which the "relative" current output from the first photodiode PD0 and second photodiode PD1; third photodiode PD2 and fourth photodiode PD3 and fifth photodiode PD4 and sixth photodiode PD5 is measured.

More specifically, a first photodiode pair is formed by the first photodiode PD0 and the second photodiode PD1. The first photodiode is held in a reverse bias state by applying a first bias voltage Vbn to its anode and applying a measurement voltage Vm1 to its cathode. The second photodiode is held in a reverse bias state by applying a second bias voltage Vbp to its cathode and applying the measurement voltage Vm1 to its anode. In accordance with the embodiments described above, Vbp>Vm>Vbn. The switching matrix 702 connects the cathode of the first photodiode PD0, the anode of the second photodiode PD1 and the first current measurement unit and connects the anode of the first photodiode PD0 and the cathode of the second photodiode PD1 to the requisite voltage input lines 704.

A second photodiode pair is formed by the third photodiode PD2 and the fourth photodiode PD3. The third photodiode PD2 is held in a reverse bias state by applying a first bias voltage Vbn to its anode and applying a measurement voltage Vm2 to its cathode. The fourth photodiode PD3 is held in a reverse bias state by applying a second bias voltage Vbp to its cathode and applying the measurement voltage Vm2 to its anode. The switching matrix 702 connects the cathode of the third photodiode PD2, the anode of the fourth photodiode PD3 and the second current measurement unit and connects the anode of the third photodiode PD2 and the cathode of the fourth photodiode PD3 to the requisite voltage input lines 704.

A third photodiode pair is formed by the fifth photodiode PD4 and the sixth photodiode PD5. The fifth photodiode PD4 is held in a reverse bias state by applying a first bias voltage Vbn to its anode and applying a measurement voltage Vm3 to its cathode. The sixth photodiode PD5 is held in a reverse bias state by applying a second bias voltage Vbp to its cathode and applying the measurement voltage Vm3 to its anode. The switching matrix 702 connects the cathode of the fifth photodiode PD4, the anode of the sixth photodiode PD5 and the third current measurement unit and connects the anode of the fifth photodiode PD4 and the cathode of the sixth photodiode PD5 to the requisite voltage input lines 704.

Figure 7C:
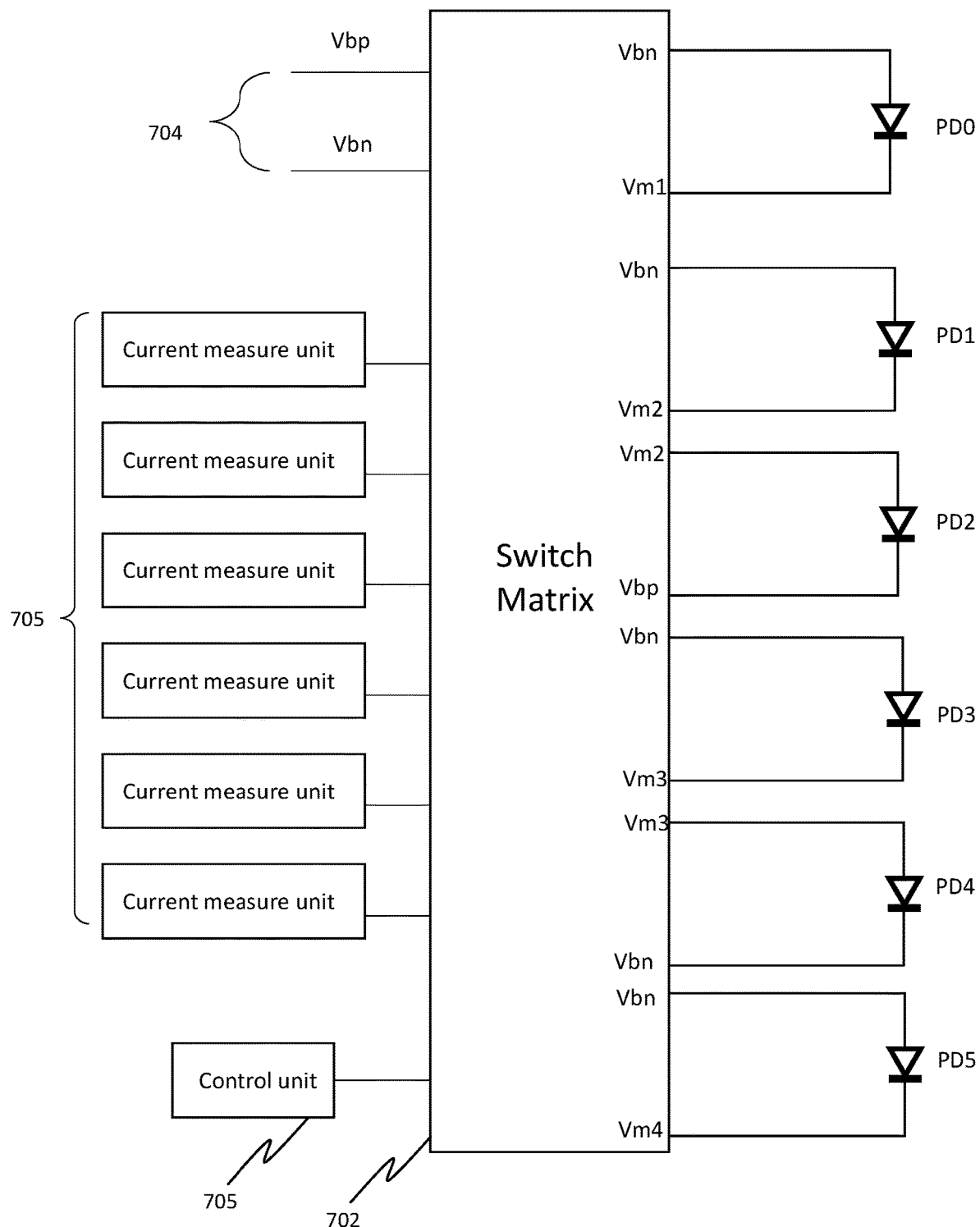
FIGS. 7c and 7d provide schematic diagrams depicting configuration of the light detection unit shown in FIG. 7a to provide a first and second "absolute" measurement mode.

FIG. 7c provides a schematic diagram showing the voltage connections necessary to implement a second configuration implementing a "relative" measurement mode in which the "relative" current output from the second photodiode PD1 and third photodiode PD2; and fourth photodiode PD3 and fifth photodiode PD4 is measured.

This configuration corresponds to that described with reference to FIG. 7b except that the photodiode pairs are formed from the second photodiode PD1 and the third photodiode PD2; and the fourth photodiode PD3 and the fifth photodiode PD4.

Figure 7D:
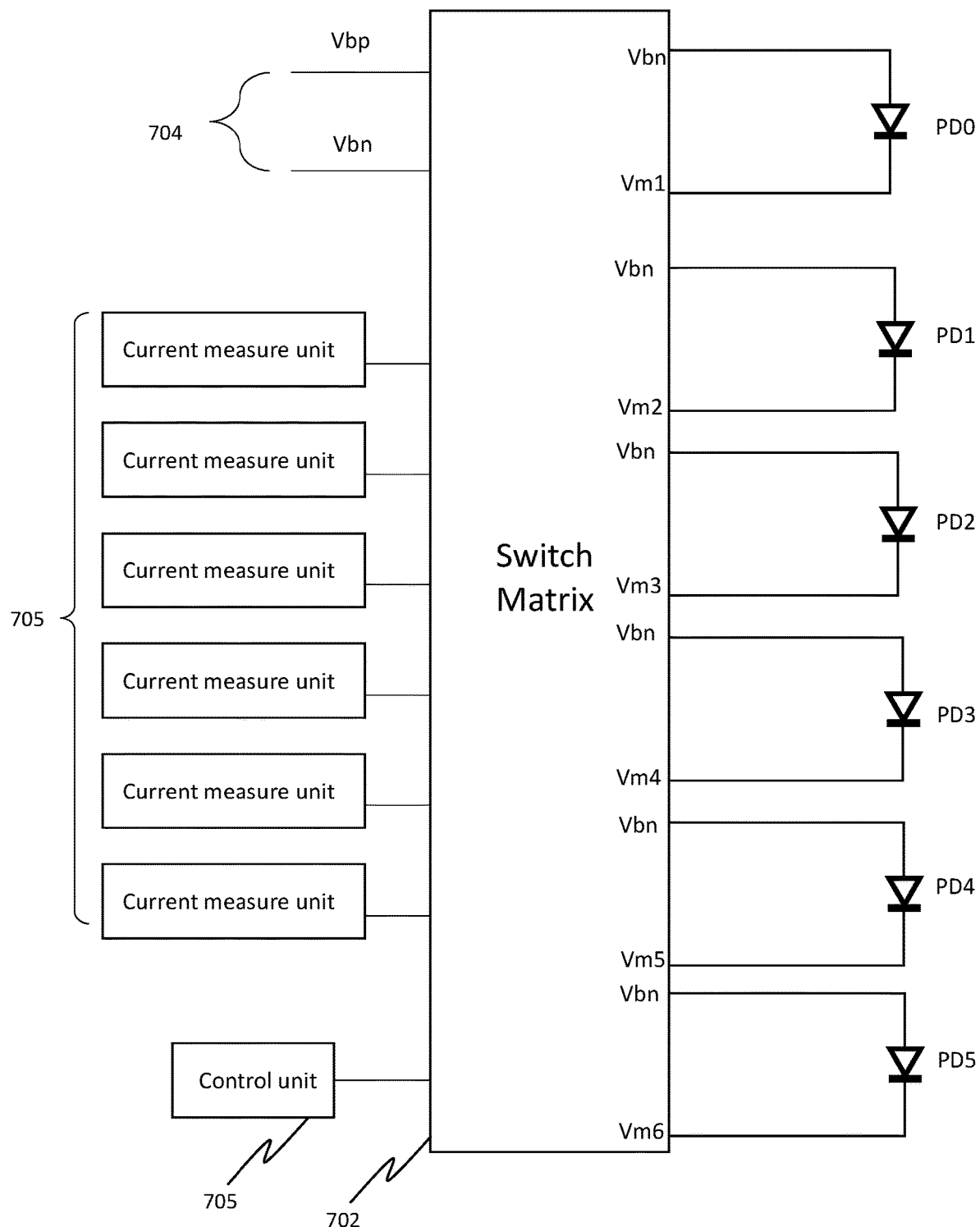

FIG. 7d provides a schematic diagram showing the voltage connections of a configuration necessary to implement an "absolute" measurement mode in which the current output from each photodiode is measured. In this configuration, the switching matrix 702 connects the first bias voltage Vbn to the anode of each photodiode connects the cathode of each photodiode to one of the measurement units (providing the measurement voltage).

The switching matrix 702 necessary to implement the configurations shown in FIGS. 7b, 7c and 7d can be provided by any suitable switching matrix as is known in the art.

Figure 8:
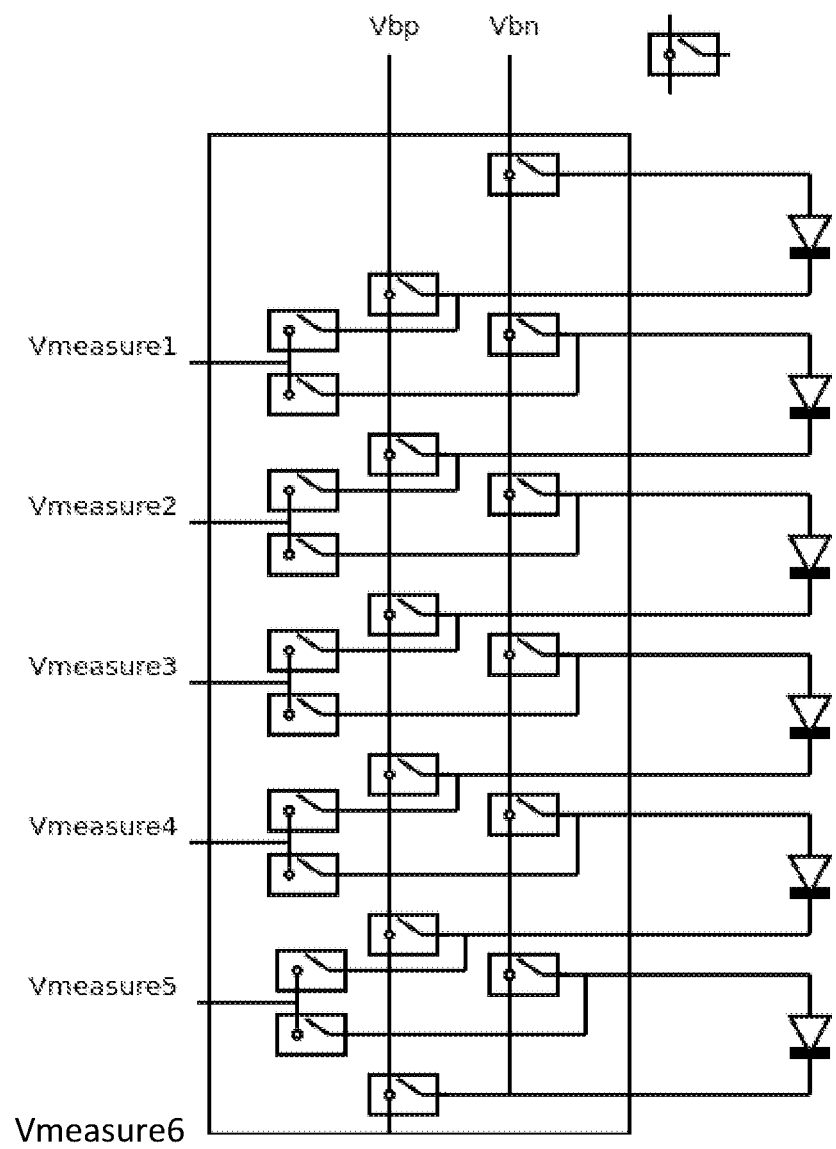
FIG. 8 provides a schematic diagram of a switching matrix for implementing a system as depicted in FIGS. 7a, 7b, 7c, 7d.

FIG. 8 provides a schematic diagram of a switching matrix arrangement designed specifically to implement the measurement configurations shown in FIGS. 7b, 7c and 7d. FIG. 8 provides a schematic diagram of such a switching matrix arrangement.

Although not shown, it will be understood that in keeping with the embodiment shown in FIG. 6, the current measurement units depicted in FIGS. 7a, 7b, 7c and 7d are connected to a memory unit in which the digital values for the current measurement are stored for onward communication to the image processing module.

In the embodiments described above, photodiodes are controlled by applying relevant bias voltages to their anodes and cathodes.

However, the characteristics of photodiodes typically vary and therefore in some embodiments, each photodiode pair for certain "relative" measurement modes (for example described with reference to FIG. 5a), and each individual photodiode for certain "absolute" measurement modes (for example described with reference to FIGS. 5b, 5c, 5h, 5i) undergo a calibration process.

During calibration, a reference light level is applied to each photodiode/photodiode pair (e.g. light level necessary to generate zero output) and bias voltages are varied until output of photodiode/photodiode pair generates the requisite output (i.e. an output corresponding to the reference light level). These "optimum" voltage bias levels are then stored and then applied to the relevant photodiodes during the imaging process.

The specific bias voltage applied during the calibration process will depend on the particular voltage configurations and physical photodiode array configurations used to implement the "relative" and "absolute" measurement modes.

For example, the calibration technique can be used to determine the bias voltages necessary to implement examples of the "relative" measurement mode. As described above, in certain embodiments the "relative" measurement mode comprises holding each photodiode pair in a reverse bias state where a first bias voltage Vbn is applied to an anode of the first photodiode of the photodiode pair and a second bias voltage Vbp is applied to a cathode of the second photodiode of the photodiode pair, and a measurement voltage Vm is applied at the cathode of the first photodiode connected to the anode of the second photodiode and the measurement voltage is a voltage level between the first bias voltage and second bias voltage. To calibrate the photodiode pairs for implementing such examples of the "relative" measurement mode, the calibration technique comprises applying reference illumination to each photodiode pair, and determining for each photodiode pair the first and second bias voltages to be applied to each photodiode pair by determining first bias voltage Vbn and second bias voltage Vbp necessary to generate a reference output current corresponding to the reference illumination. These determined first and second voltages are then stored.

Correspondingly, the calibration technique can be used to determine the bias voltages necessary to implement examples of the "absolute" measurement mode. As described above, in certain embodiments the "absolute" measurement mode comprises applying a null voltage Vbx to the anode of the first photodiode of each pair thereby holding the first photodiode of each pair in an unbiased, non-conducting state, and applying a first bias voltage Vbp to the cathode of the second photodiode of each pair and applying the measurement voltage Vm at the cathode of the first photodiode connected to the anode of the second photodiode, thereby holding the second photodiode of each photodiode pair in a reverse bias state, and, before or subsequently applying a second bias voltage Vbn to the anode of the first photodiode of each pair and the measurement voltage Vm at the cathode of the first photodiode connected to the anode of the second photodiode thereby holding the first photodiode of each pair in a reverse biased state, and applying a null voltage Vbx to the cathode of the second photodiode of each photodiode pair thereby holding the second photodiode of each photodiode pair in an unbiased, non-conducting state.

To calibrate the photodiode pairs for implementing such examples of the "absolute" measurement mode the calibration technique comprises applying reference illumination to each photodiode pair, and for each photodiode pair: applying a null voltage to the anode of the first photodiode of the photodiode pair and determining the first bias voltage Vbp necessary to be applied to the cathode of the second photodiode necessary to generate a reference output from the second photodiode corresponding to the reference illumination, and before or subsequently, applying a null voltage to the cathode of the second photodiode of the photodiode pair and determining the second bias voltage Vbn necessary to be applied to the anode of the first photodiode necessary to generate a reference output from the first photodiode corresponding to the reference illumination. These determined first and second voltages are then stored.

To apply the stored voltages, typically the voltage input lines (e.g. lines 602 shown in FIG. 6 and lines 704 shown in FIGS. 7a to 7d) are sequentially connected to programmable voltage sources which are controlled by the control unit to change the supplied voltage in dependence on which photodiodes/photodiode pairs are currently connected.

In certain embodiments, determining the first bias voltage and the second bias voltage for each photodiode pair in each measurement mode comprises modulating between a first voltage level and a second voltage level of a plurality of predetermined voltage levels. Typically, the number of voltage levels that can be produced by the programmable voltage sources may be limited therefore, during the calibration process, whichever of the available voltage levels results in an output closest to the requisite output are selected. In certain embodiments, during calibration, it can be identified that the "ideal" bias voltage level (i.e. that necessary to apply to the photodiode pairs/photodiode to generate the requisite output given the input reference light level) may be between two of the available voltage levels.

In such cases, in certain embodiments, in use, the programmable voltage sources are arranged to modulate between the two voltage levels which the ideal bias voltage is between.

A specific example of this is described below with reference to FIG. 9.

Figure 9:
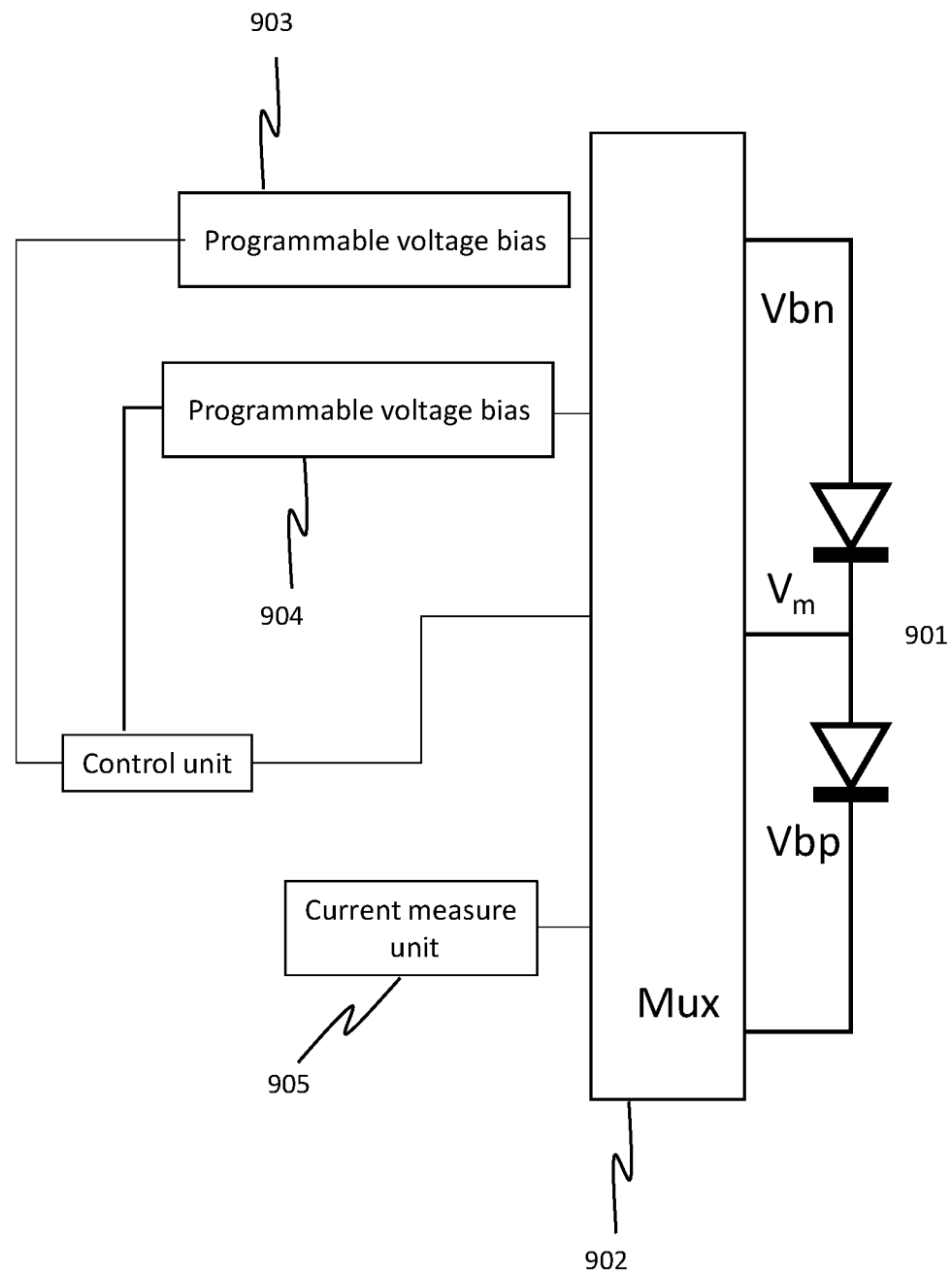
FIG. 9 provides a schematic diagram illustrate a calibration technique in accordance with certain embodiments of the invention, and FIG. 10 provides a schematic diagram of an imaging matrix in accordance with certain embodiments of the invention.

FIG. 9 provides a schematic diagram of part of a light detection unit. For simplicity, only one photodiode pair is shown, but it will be understood that typically the photodiode array comprises multiple photodiode pairs.

The input voltage node connected to the anode of the first photodiode of the photodiode pair 901 is connected via the switching matrix 902 to a first programmable voltage bias unit 903. The input voltage node connected to the cathode of the second photodiode of the photodiode pair 901 is connected via the switching matrix 902 to a second programmable voltage bias unit 904. The voltage node at the cathode of the first photodiode and the anode of the second photodiode (where the measurement voltage is applied) is connected to a current measure unit 905 (as described with reference to FIG. 6, the current measure unit 905 is typically connected to a memory unit, however this is omitted in FIG. 9 for clarity).

As described above, in operation, to measure the difference in the current through the first photodiode of the photodiode pair 901, and the current through the second photodiode of the photodiode pair 901, a first bias voltage Vbn is applied to the anode of the first photodiode of the photodiode pair 601, and a second bias voltage Vbp is applied to the cathode of the second photodiode of the photodiode pair. The application of the measurement voltage Vm which is between the first bias voltage Vbn and the second bias voltage Vbp reverse biases both photodiodes and a measurement current is generated which is the difference between the current flowing through the first photodiode and the current flowing through the second photodiode.

However, variances between the first and second photodiode (for example variances in internal resistance, capacitance and forward voltage) will mean that in the reverse bias configuration, the photodiodes are likely to produce different amounts of current for the same light level. The programmable voltage bias units 903, 904 are arranged to compensate for these variances by altering the voltage biases to accommodate for these differences.

To implement this technique, typically, each photodiode pair 901 undergoes a calibration cycle before the photodiode is used.

In one exemplary calibration mode, illumination of a predetermined intensity (a reference intensity) is directed at the photodiode pair 901 and a number of pre-set voltage level combinations are sequentially applied via the programmable voltage bias units 903, 904 to determine which voltage bias combinations results in a zero current measure measured at the current measure unit 905.

For example, there may be four pre-set voltage levels for Vbn ($Vbn_1$, $Vbn_2$, $Vbn_3$ and $Vbn_4$) and four pre-set voltage levels for Vbp ($Vbp_1$, $Vbp_2$, $Vbp_3$ and $Vbp_4$). During the calibration phase, each of the possible voltage level combinations is tried to determine which combination results in the required current output (e.g. zero current output). There would be 16 possible voltage combinations in such an example:

| | | | |
|---|---|---|---|
| $Vbn_1$ and $Vbp_1$ | $Vbn_2$ and $Vbp_1$ | $Vbn_3$ and $Vbp_1$ | $Vbn_4$ and $Vbp_1$ |
| $Vbn_1$ and $Vbp_2$ | $Vbn_2$ and $Vbp_2$ | $Vbn_3$ and $Vbp_2$ | $Vbn_4$ and $Vbp_2$ |
| $Vbn_1$ and $Vbp_3$ | $Vbn_2$ and $Vbp_3$ | $Vbn_3$ and $Vbp_3$ | $Vbn_4$ and $Vbp_3$ |
| $Vbn_1$ and $Vbp_4$ | $Vbn_2$ and $Vbp_4$ | $Vbn_3$ and $Vbp_4$ | $Vbn_4$ and $Vbp_4$ |

In certain situations, it may be determined that one of the optimum voltages lies between a first and second of the pre-set voltages. In such situations, the programmable voltage bias units 703, 704 can be arranged, during operation to modulate between the first and second pre-set voltage.

For example, during calibration it may be determined that a combination of a $Vbn_2$ and $Vbp_2$ gives a current of $+Ic_{min}$ and $Vbn_2$ and $Vbp_3$ gives a current of $-Ic_{min}$. Where $Ic_{min}$ is the lowest current level measured. In such cases, it may be determined that the optimum voltage bias for the first programmable voltage bias unit 703 is to provide a voltage bias of $Vbn_2$, and the second programmable voltage bias unit 704 to modulate between $Vbp_2$ and $Vbp_3$.

It will be understood that a similar calibration technique can be performed for each photodiode for "absolute" measurement modes described above.

Figure 10:
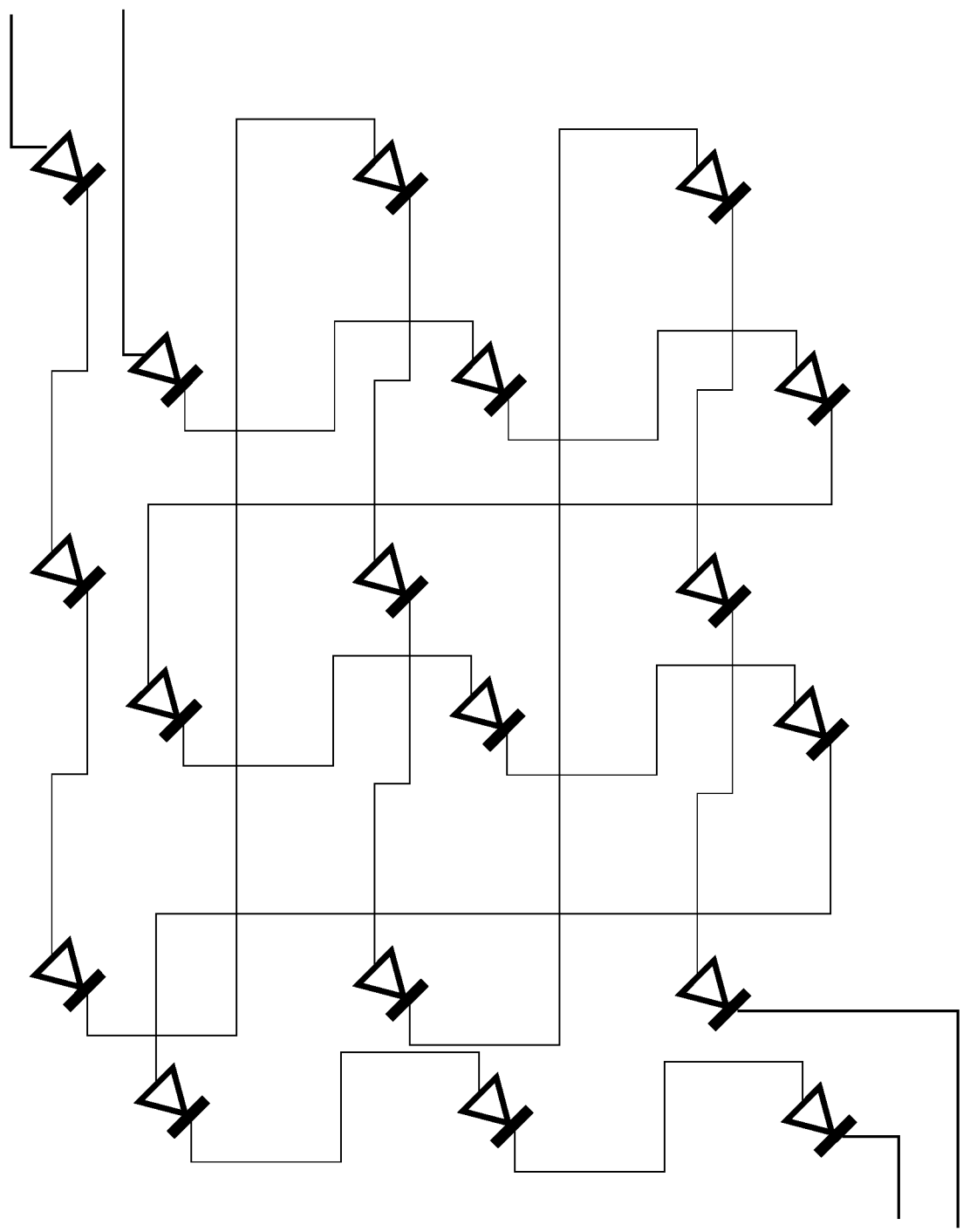

As described above, in certain examples the photodiodes of the photodiode array can be arranged in series (for example in pairs of alternating polarity, or with the same polarity). In the examples described above, the number of photodiodes in the array is small (e.g. six photodiodes) to simplify explanation of the operation of different configurations of the array. However, it will be understood that the photodiode array in typical implementations comprises many more photodiodes. The photodiode array can be of any suitable length for example 50 photodiodes in an array. In certain examples, a first photodiode array and second photodiode array thus arranged can be used to form a 2D imaging matrix. An example of such an arrangement is shown in FIG. 10.

For clarity, the voltage node connections in between adjacent photodiodes are not shown.

It will be understood that in embodiments of the invention, data processing components can be implemented using any suitable electronic processing and signal processing means of the type well known in the art. For example, the control module, control unit and image processing module of the near-infrared spectroscopy apparatus and the light detection units, described, for example, with reference to FIGS. 1 and 2, can be implemented by one or more suitably configured microprocessors or suitably configured integrated circuits.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope of the present disclosure. Accordingly, the various embodiments disclosed herein are not intended to be limiting, with the true scope being indicated by the following claims.

The invention claimed is:

1. A method of measuring light intensity for imaging using a light detector array comprising a plurality of light detectors, each light detector of the plurality of light detectors arranged to generate an output corresponding to an intensity of incident light, said method comprising, in a first measurement mode:
    controlling the light detector array to generate a first plurality of output signals, each output signal of the first plurality of output signals generated by one of a plurality of groups of proximate light detectors of the light detector array, each group of proximate light detectors comprising a first light detector and second light detector forming a light detector pair, each output signal of the first plurality of output signals corresponding to a difference between the light intensity detected by the light detectors of the group of proximate light detectors, and generating a light intensity measurement for each group from each received output signal of the first plurality of output signals, the method further comprising, in a second measurement mode:

controlling the light detector array to generate a second plurality of output signals, each output signal of the second plurality of output signals generated by one of the light detectors, and generating a light intensity measurement for each light detector from each received output signal of the second plurality of output signals.

2. A method according to claim 1, wherein the light detectors comprise photodiodes.

3. A method according to claim 2, wherein the photodiodes of the light detector array are arranged in a linear array.

4. A method according to claim 3, wherein each light detector pair comprise a photodiode pair comprising a first photodiode in series with a second photodiode.

5. A method according to claim 4, wherein the anode and cathode of each photodiode are connected, via a switching matrix to a plurality of voltage lines and measurement lines to implement the first and second measurement mode.

6. A method according to claim 4, wherein the linear array of light detectors comprises a plurality of photodiode pairs connected in series.

7. A method according to claim 6, wherein a cathode of the first photodiode of each photodiode pair is connected to an anode of the second photodiode of each pair.

8. A method according to claim 7, wherein the photodiode pairs of the linear array are arranged in sequentially forward and reverse polarity.

9. A method according to claim 8, wherein the first measurement mode is implemented by:

holding each photodiode pair in a reverse bias state where a first bias voltage Vbn is applied to an anode of the first photodiode of the photodiode pair and a second bias voltage Vbp is applied to a cathode of the second photodiode of the photodiode pair, and a measurement voltage Vm is applied at the cathode of the first photodiode connected to the anode of the second photodiode, said measurement voltage a voltage level between the first bias voltage and second bias voltage, and measuring an output of each photodiode pair corresponding to a difference in the light detected of the photodiode pair by measuring the current output at the cathode of the first photodiode connected to the anode of the second photodiode.

10. A method according to claim 9, wherein the second measurement mode is implemented by:

applying a null voltage Vbx to the anode of the first photodiode of each pair thereby holding the first photodiode of each pair in an unbiased, non-conducting state, and applying the second bias voltage Vbp to the cathode of the second photodiode of each pair and applying the measurement voltage Vm at the cathode of the first photodiode connected to the anode of the second photodiode, thereby holding the second photodiode of each photodiode pair in a reverse bias state, and measuring an output of the second photodiode of each photodiode pair from the current output measured at the cathode of the first photodiode connected to the anode of the second photodiode, and, before or subsequently applying a first bias voltage Vbn to the anode of the first photodiode of each pair and applying the measurement voltage Vm at the cathode of the first photodiode connected to the anode of the second photodiode thereby holding the first photodiode of each pair in a reverse biased state, and applying a null voltage Vbx to the cathode of the second photodiode of each photodiode pair thereby holding the second photodiode of each photodiode pair in an unbiased, non-conducting state, and measuring an output of the second photodiode of each photodiode pair from the current output measured at the cathode of the first photodiode connected to the anode of the second photodiode.

11. A method according to claim 7, wherein the photodiode pairs of the linear array are arranged with the same polarity.

12. A method according to claim 11, wherein the first measurement mode is implemented by:

holding each photodiode pair in a null bias state where a zero voltage bias is applied to the anode and cathode of each of photodiode, and measuring an output of each photodiode pair corresponding to a difference in the light detected of the photodiode pair by measuring the current output at the cathode of the first photodiode connected to the anode of the second photodiode.

13. A method according to claim 11, wherein the first mode is implemented by:

holding each photodiode pair in a reverse bias state where a sequentially increasing voltage bias is applied to the anode of each adjacent photodiode, and measuring an output of each photodiode pair corresponding to a difference in the light detected of the photodiode pair by measuring the current output at the cathode of the first photodiode connected to the anode of the second photodiode.

14. A method according to claim 11, wherein the second measurement mode is implemented by:

applying a first bias voltage to the anode of first photodiode of each pair;

applying the first bias voltage to the cathode of the first diode of each pair and the anode of the second photodiode of each pair, thereby holding the first photodiode of each pair in an unbiased, non-conducting state, wherein the first bias voltage sequentially increases along the photodiode array for each photodiode pair thereby holding the second photodiode of each pair in a reverse bias state, and measuring an output of the second photodiode of each photodiode pair from the current output measured at the cathode of the first photodiode connected to the anode of the second photodiode, and, before or subsequently applying the first bias voltage to the cathode of the second photodiode of each pair;

applying the same bias voltage to the cathode of the first diode of each pair and the anode of the second photodiode of each pair, thereby holding the second photodiode of each pair in an unbiased, non-conducting state, wherein the second bias voltage sequentially increases along the photodiode array for each photodiode pair thereby holding the first photodiode of each pair in a reverse bias state, and measuring an output of the first photodiode of each photodiode pair from the current output measured at the cathode of the first photodiode connected to the anode of the second photodiode.

15. A method according to claim 9, comprising
applying a requisite voltages to the anodes and cathodes of the photodiodes by connecting the anodes and cathodes of the photodiodes to a plurality of voltage lines, each voltage line held at one of the requisite voltages.

16. A method according to claim 15, wherein the anodes and cathodes of the photodiodes are connectable to the requisite voltage lines via a switching matrix.

17. A method according to claim 16, wherein each voltage line is connected to a programmable voltage supply arranged to provide for each photodiode pair and for each photodiode a voltage level corresponding to the first bias voltage Vbn or second bias voltage Vbp, the first bias voltage Vbn and second bias voltage Vbp determined for each photodiode pair and for each photodiode in accordance with a calibration technique.

18. A method according to claim 17, wherein the calibration technique comprises
applying reference illumination to each photodiode and each photodiode pair
determining, for operation in the first measurement mode, the first and second bias voltages by determining first and second voltages necessary to generate a reference output current corresponding to the reference illumination, and
determining for operation in the second measurement mode, first and second bias voltages necessary to generate a reference output current corresponding to the reference illumination.

19. A method according to claim 17, wherein
one or more of the first and second bias voltages necessary to generate a reference output current corresponding to the reference illumination for operation in the first measurement mode, and/or
one or more of the first and second bias voltages necessary to generate a reference output current corresponding to the reference illumination for operation in the second measurement mode are provided by the programmable voltage supplies by modulating between a first and second voltage level.

20. A method according to claim 1, further comprising generating near-infrared spectroscopy imaging data using the light intensity measurements.

21. An imaging apparatus comprising:
a light detector array comprising a plurality of light detectors, each light detector of the plurality of light detectors operable to generate an output corresponding to an intensity of incident light, said apparatus comprising means to control the plurality of light detectors, in a first measurement mode:
to generate a first plurality of output signals, each output signal of the first plurality of output signals generated by one of a plurality of groups of proximate light detectors of the light detector array, wherein each group of proximate light detectors comprises a first light detector and second light detector forming a light detector pair, each output signal of the first plurality of output signals corresponding to a difference between the light intensity detected by the light detectors of the group of proximate light detectors, said apparatus further comprising a light intensity measurement unit arranged to generate a light intensity measurement for each group from each received output signal of the first plurality of output signals, wherein
the means to control the plurality of light detectors is operable, in a second measurement mode:
to control the plurality of light detectors to generate a second plurality of output signals, each output signal of the second plurality of output signals generated by one of the light detectors, and
the light intensity measurement unit is arranged to generate a light intensity measurement for each light detector from each received output signal of the second plurality of output signals.

22. An imaging apparatus according to claim 21, wherein the light detectors comprise photodiodes.

23. An imaging apparatus according to claim 22, wherein the photodiodes of the light detector array are arranged in a linear array.

24. An imaging apparatus according to claim 23, wherein each light detector pair comprise a photodiode pair comprising a first photodiode in series with a second photodiode.

25. An imaging apparatus according to claim 24, wherein the anode and cathode of each photodiode are connected, via a switching matrix to a plurality of voltage lines and measurement lines to implement the first and second measurement mode.

26. An imaging apparatus according to claim 25, wherein the linear array of light detectors comprises a plurality of photodiode pairs connected in series.

27. An imaging apparatus according to claim 26, wherein a cathode of the first photodiode of each photodiode pair is connected to an anode of the second photodiode of each pair.

28. An imaging apparatus according to claim 27, wherein the photodiode pairs of the linear array are arranged in sequentially forward and reverse polarity.

29. An imaging apparatus according to claim 28, wherein the first measurement mode is implemented by the means to control the plurality of light detectors:
holding each photodiode pair in a reverse bias state where a first bias voltage Vbn is applied to an anode of the first photodiode of the photodiode pair and a second bias voltage Vbp is applied to a cathode of the second photodiode of the photodiode pair, and a measurement voltage Vm is applied at the cathode of the first photodiode connected to the anode of the second photodiode said measurement voltage a voltage level between the first bias voltage and second bias voltage, and
the light intensity measurement unit is arranged to measure an output of each photodiode pair corresponding to a difference in the light detected of the photodiode pair by measuring the current output at the cathode of the first photodiode connected to the anode of the second photodiode.

30. An imaging apparatus according to claim 29, wherein the second measurement mode is implemented by the means to control the plurality of light detectors:
applying a null voltage Vbx to the anode of the first photodiode of each pair thereby holding the first photodiode of each pair in an unbiased, non-conducting state, and applying the second bias voltage Vbp to the cathode of the second photodiode of each pair and applying the measurement voltage Vm at the cathode of the first photodiode connected to the anode of the second photodiode, thereby holding the second photodiode of each photodiode pair in a reverse bias state, and the light intensity measurement unit is arranged to measure an output of the second photodiode of each photodiode pair from the current output measured at the cathode of the first photodiode connected to the anode of the second photodiode, and, before or subsequently the means to control the plurality of light detectors:

applying a first bias voltage Vbn to the anode of the first photodiode of each pair and applying the measurement voltage Vm at the cathode of the first photodiode connected to the anode of the second photodiode thereby holding the first photodiode of each pair in a reverse biased state, and applying a null voltage Vbx to the cathode of the second photodiode of each photodiode pair thereby holding the second photodiode of each photodiode pair in an unbiased, non-conducting state, the light intensity measurement unit is arranged to measure an output of the second photodiode of each photodiode pair from the current output measured at the cathode of the first photodiode connected to the anode of the second photodiode.

31. An imaging apparatus according to claim 27, wherein the photodiode pairs of the linear array are arranged with the same polarity.

32. An imaging apparatus according to claim 31, wherein the first measurement mode is implemented by the means to control the plurality of light detectors:

holding each photodiode pair in a null bias state where a zero voltage bias is applied to the anode and cathode of each of photodiode, and the light intensity measurement unit is arranged to measure an output of each photodiode pair corresponding to a difference in the light detected of the photodiode pair by measuring the current output at the cathode of the first photodiode connected to the anode of the second photodiode.

33. An imaging apparatus according to claim 31, wherein the first mode is by the means to control the plurality of light detectors:

holding each photodiode pair in a reverse bias state where a sequentially increasing voltage bias is applied to the anode of each adjacent photodiode, and the light intensity measurement unit is arranged to measure an output of each photodiode pair corresponding to a difference in the light detected of the photodiode pair by measuring the current output at the cathode of the first photodiode connected to the anode of the second photodiode.

34. An imaging apparatus according to claim 31, wherein the second mode is implemented by the means to control the plurality of light detectors:

applying a first bias voltage to the anode of first photodiode of each pair;

applying the first bias voltage to the cathode of the first diode of each pair and the anode of the second photodiode of each pair, thereby holding the first photodiode of each pair in an unbiased, non-conducting state, wherein the first bias voltage sequentially increases along the photodiode array for each photodiode pair thereby holding the second photodiode of each pair in a reverse bias state, and the light intensity measurement unit is arranged to measure an output of the second photodiode of each photodiode pair from the current output measured at the cathode of the first photodiode connected to the anode of the second photodiode, and, before or subsequently the means to control the plurality of light detectors:

applying the first bias voltage to the cathode of the second photodiode of each pair;

applying the same bias voltage to the cathode of the first diode of each pair and the anode of the second photodiode of each pair, thereby holding the second photodiode of each pair in an unbiased, non-conducting state, wherein the second bias voltage sequentially increases along the photodiode array for each photodiode pair thereby holding the first photodiode of each pair in a reverse bias state, and the light intensity measurement unit is arranged to measure an output of the first photodiode of each photodiode pair from the current output measured at the cathode of the first photodiode connected to the anode of the second photodiode.

35. An imaging apparatus according to claim 29, wherein the means to control the plurality of light detectors is operable to apply the requisite voltages to the anodes and cathodes of the photodiodes by connecting the anodes and cathodes of the photodiodes to a plurality of voltage lines, each voltage line held at one of the requisite voltages.

36. An imaging apparatus according to claim 35, wherein the means to control the plurality of light detectors comprises a switching matrix controlled by a control unit.

37. A near-infrared spectroscopy system for imaging a subject's head comprising an imaging apparatus according to claim 21.

* * * * *